US012709617B2

(12) United States Patent
Beresis et al.

(10) Patent No.: US 12,709,617 B2
(45) Date of Patent: Aug. 18, 2026

(54) OXYGEN-CONTAINING HETEROCYCLIC COMPOUND AND USE THEREOF

(71) Applicants: Icahn School of Medicine at Mount Sinai, New York, NY (US); THE UNITED STATES GOVERNMENT AS REPRESENTED BY THE DEPARTMENT OF VETERANS AFFAIRS, Washington, DC (US)

(72) Inventors: Richard T. Beresis, San Francisco, CA (US); John Cijiang He, Forest Hills, NY (US); Kyung Lee, Bronx, NY (US)

(73) Assignees: Icahn School of Medicine at Mount Sinai, New York, NY (US); The United States Government as Represented by the Dept. of Veterans Affairs, Washington, DC (US)

( * ) Notice: Subject to any disclaimer, the term of this patent is extended or adjusted under 35 U.S.C. 154(b) by 577 days.

(21) Appl. No.: 18/365,473

(22) Filed: Aug. 4, 2023

(65) Prior Publication Data

US 2024/0051965 A1 Feb. 15, 2024

Related U.S. Application Data

(60) Provisional application No. 63/370,516, filed on Aug. 5, 2022.

(51) Int. Cl.
*C07D 491/052* (2006.01)

(52) U.S. Cl.
CPC ................................ *C07D 491/052* (2013.01)

(58) Field of Classification Search
None
See application file for complete search history.

(56) References Cited

U.S. PATENT DOCUMENTS 10,669,266 B2 6/2020 He et al.
2010/0168005 A1 7/2010 Bolli et al.
2010/0174065 A1 7/2010 Heer et al.
2011/0274657 A1 11/2011 Izquierdo et al.
2019/0352292 A1 11/2019 He et al.
2021/0047340 A1 * 2/2021 Green ................ C07D 491/056

FOREIGN PATENT DOCUMENTS

WO 2018231745 A1 12/2018
WO 2022173795 A1 8/2022

OTHER PUBLICATIONS

Pubchem, Substance Record for SID 379155454, Modify Date: Jun. 3, 2019 [retrieved on Oct. 18, 2023]. Retrieved from the Internet: <URL: https://pubchem.ncbi.nlm.nih.gov/substance/379155454>.

* cited by examiner

*Primary Examiner* — Kortney L. Klinkel
*Assistant Examiner* — Steve H. Drouin
(74) *Attorney, Agent, or Firm* — Heslin Rothenberg Farley & Mesiti P.C.

(57) ABSTRACT

Disclosed is an oxygen-containing heterocyclic compound, and use thereof. The present disclosure provides an oxygen-containing heterocyclic compound represented by Formula I, a pharmaceutically acceptable salt thereof, deuterated derivative thereof, a solvate thereof, a solvate of the pharmaceutically acceptable salt thereof or a crystal form thereof, and the oxygen-containing heterocyclic compound is expected to selectively inhibit Smad3 activation.

I

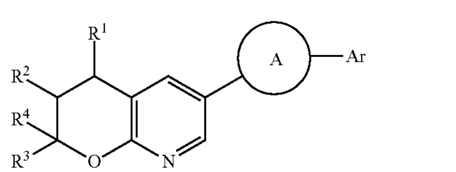

15 Claims, No Drawings

OXYGEN-CONTAINING HETEROCYCLIC COMPOUND AND USE THEREOF

CROSS-REFERENCE TO RELATED APPLICATION

This application claims priority of U.S. provisional application 63/370,516, filed Aug. 5, 2022, the disclosure of which is hereby incorporated herein by reference in its entirety.

FIELD OF THE DISCLOSURE

This disclosure relates to oxygen-containing heterocyclic compound and use thereof.

BACKGROUND OF THE DISCLOSURE

Fibrosis is characterized by excessive production and accumulation of extracellular matrix proteins, which leads to progressive loss of tissue function and eventual organ failure. Chronic kidney diseases, irrespective of primary insults, are usually accompanied by kidney interstitial fibrosis. Therapeutic strategy for chronic kidney disease, in order to halt decline of kidney function, requires not only removal of the causal factors, such as hyperglycemia, hypertension, and HIV infection, but also anti-fibrosis therapy to restore the normal kidney structure and function. A number of other organ-specific fibrotic disorders are known, in addition to kidney fibrosis, including liver, cardiac and pulmonary fibrosis.

Renal fibrosis is considered the final convergent pathway for progressive chronic kidney disease, regardless of the original etiologies of the disease. Although much has been learned of the molecular mechanisms underlying renal fibrogenesis, there is still a paucity of success in translating this knowledge to clinical application. It has been demonstrated that HIPK2 is a multifunctional activator of TGF-β/Smad3, NF-κB, and p53 pathways and that the global knockout of HIPK2 in mice attenuated kidney fibrosis in vivo. U.S. Pat. No. 10,669,266 discloses small molecule inhibitors of HIPK2 that specifically block TGF-β/Smad3 pathway to attenuate renal fibrosis without causing adverse systemic effects. However, solubility and potency issues remain with the compounds disclosed in the '266 patent.

Transforming growth factor-β1 (TGF-β1) has been identified to be the most important pro-fibrogenic factor for kidney disease. TGF-β1 binds to type II TGF-β receptor, allowing its dimerization with type I TGF-β receptor and leading to phosphorylation of Smad2 and Smad3. Phosphorylated Smad3 relocates into nuclei, thereby binds to Smad binding element in promoter and activating the transcription of the target genes including pro-fibrotic genes such as collagen I, fibronectin, and alpha-smooth muscle actin (α-SMA). It is known that Smad3 is highly activated in fibrotic kidney and that knockout of Smad3 attenuates kidney fibrosis in animal models of kidney disease. Blockade of TGF-β1/Smad3 pathway therefore provides a therapeutic strategy for kidney fibrosis.

CONTENT OF THE DISCLOSURE

The technical problem to be solved in the present disclosure is the lack of effective drugs serving as Smad3 activation inhibitors for clinical treatment in the prior art. Therefore, the present disclosure provides oxygen-containing heterocyclic compound and use thereof that can selectively inhibit Smad3 activation.

The present disclosure solves the above-mentioned technical problem through the following technical solutions.

The present disclosure provides an oxygen-containing heterocyclic compound represented by Formula I, a pharmaceutically acceptable salt thereof, deuterated derivative thereof, a solvate thereof, a solvate of the pharmaceutically acceptable salt thereof or a crystal form thereof:

I

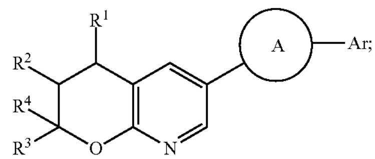

Wherein:

Ar is $C_{6-20}$ aryl, $C_{6-20}$ aryl substituted with one or more $R^{1-1}$, "5-12 membered heteroaryl containing 1-4 heteroatoms selected from O, S and N", or "5-12 membered heteroaryl containing 1-4 heteroatoms selected from O, S and N" substituted with one or more $R^{1-2}$;

$R^{1-1}$ and $R^{1-2}$ are independently selected from halogen, hydroxyl and $C_{1-6}$ alkyl;

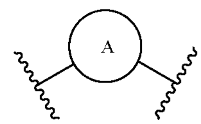

is a 5-6 membered heteroaryl containing 1-3 heteroatoms selected from O, S and N;

$R^1$ and $R^2$ are independently selected from hydrogen, deuterium, hydroxyl, $C_{1-6}$ alkyl, amino, and $—OC_{1-6}$ alkyl;

$R^3$ and $R^4$ are $C_{1-6}$ alkyl substituted with deuterium, or, $R^3$ and $R^4$ together with the atom they are attached form $C_{3-8}$ cycloalkyl, $C_{3-8}$ cycloalkyl substituted with $R^{1-3}$, 4- to 10-membered heterocycloalkyl containing 1-3 heteroatoms selected from O, S and N, "4- to 10-membered heterocycloalkyl containing 1-3 heteroatoms selected from O, S and N" substituted with $R^{1-4}$;

$R^{1-3}$ and $R^{1-4}$ are independently selected from halogen, deuterium, hydroxyl and $C_{1-6}$ alkyl.

In a certain embodiment, the oxygen-containing heterocyclic compound represented by Formula I has the structure of Formula II:

II

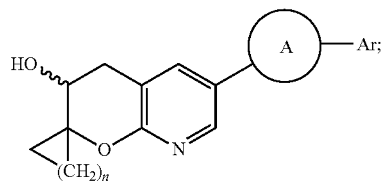

Wherein 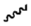 represents 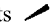,  or a mixture of 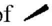 and 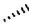;

n is 1, 2, 3, 4 or 5;

Ar and

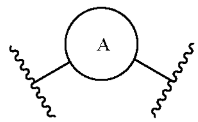

are defined as the Formula I.

In a certain embodiment, the oxygen-containing heterocyclic compound represented by Formula I has the structure of Formula III:

III

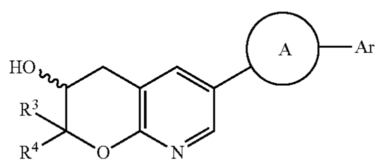

Wherein:

Ar and

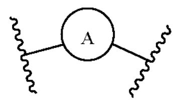

are defined as the Formula I;

represents , or a mixture of and ;

$R^3$ and $R^4$ are $C_{1-6}$ alkyl substituted with deuterium.

In a certain embodiment, the formula III has the following structure:

III'

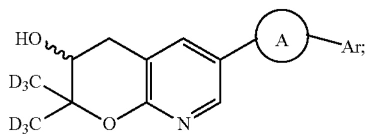

Wherein, , Ar and

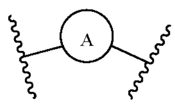

are defined as the formula III.

In a certain embodiment, in the formula II or III',

Ar is $C_{6-20}$ aryl substituted with one or more $R^{1-1}$, or "5-12 membered heteroaryl containing 1-4 heteroatoms selected from O, S and N" substituted with one or more $R^{1-2}$;

$R^{1-1}$ and $R^{1-2}$ are independently selected from halogen and $C_{1-6}$ alkyl;

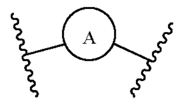

is a 5-6 membered heteroaryl containing 1-3 heteroatoms selected from O, S and N;

represents or ;

n is 2 or 3.

In a certain embodiment, in the formula II,

Ar is $C_{6-20}$ aryl substituted with one or more $R^{1-1}$, or "5-12 membered heteroaryl containing 1-4 heteroatoms independently selected from O, S and N" substituted with one or more $R^{1-2}$;

$R^{1-1}$ and $R^{1-2}$ independently selected from halogen and $C_{1-6}$ alkyl;

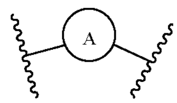

is 5-6 membered heteroaryl containing 1-3 heteroatoms independently selected from O, S and N;

represents or ;

n is 2 or 3.

In a certain embodiment, in the formula II or III',

Ar is $C_{6-20}$ aryl substituted with one or more $R^{1-1}$;

$R^{1-1}$ is halogen;

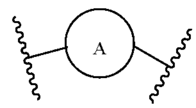

is a 5-6 membered heteroaryl containing 1-3 heteroatoms selected from O, S and N;

represents or ;

n is 2.

In a certain embodiment, n is 1, 2 or 3.

In a certain embodiment, Ar is $C_{6-20}$ aryl substituted with one or more $R^{1-1}$ or "5-12 membered heteroaryl containing 1-4 heteroatoms independently selected from O, S and N" substituted with one or more $R^{1-2}$.

In a certain embodiment, $R^{1-1}$ and $R^{1-2}$ are independently selected from halogen, and $C_{1-6}$ alkyl;

In a certain embodiment,

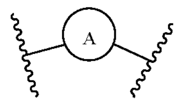

is a 5 membered heteroaryl containing 3 heteroatoms selected from O and N.

In a certain embodiment, $R^3$ and $R^4$ together with the atom they are attached form a 3-8 membered cyclic ring.

In a certain embodiment, when Ar is $C_{6-20}$ aryl, or $C_{6-20}$ aryl substituted with one or more $R^{1-1}$, the $C_{6-20}$ aryl and the $C_{6-20}$ aryl in the $C_{6-20}$ aryl substituted with one or more $R^{1-1}$ are $C_{6-10}$ aryl; the $C_{6-10}$ aryl is phenyl or naphthyl;

In a certain embodiment, when Ar is "5-12 membered heteroary containing 1-4 heteroatoms independently selected from O, S and N", or "5-12 membered heteroary containing 1-4 heteroatoms independently selected from O, S and N" substituted with one or more $R^{1-2}$, the "5-12 membered heteroary containing 1-4 heteroatoms independently selected from O, S and N" and "5-12 membered heteroary containing 1-4 heteroatoms independently selected from O, S and N" in the "5-12 membered heteroary containing 1-4 heteroatoms independently selected from O, S and N" substituted with one or more $R^{1-2}$ are "5 membered heteroary containing 2 heteroatoms selected from N", for example, pyrazolyl ( 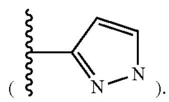 ).

In a certain embodiment, when

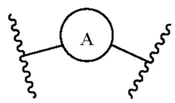

is a 5-6 membered heteroary containing 1-3 heteroatoms independently selected from O and N, the

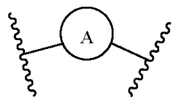

is a 5 membered heteroary containing 3 heteroatoms independently selected from O and N, for example,

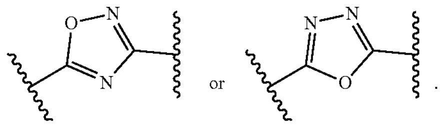 [SMILES: *c1noc(*)n1 ; *c1nnc(*)o1]

In a certain embodiment, when $R^{1-1}$ and $R^{1-2}$ independently selected from halogen, then the halogen is —F, —Cl, —Br or —I.

In a certain embodiment, when $R^{1-1}$ and $R^{1-2}$ independently selected from $C_{1-6}$ alkyl, then the $C_{1-6}$ alkyl is $C_{1-4}$ alkyl, or may be methyl, ethyl, n-propyl, isopropyl, n-butyl, isobutyl, sec-butyl or tert-butyl, or may be methyl.

In a certain embodiment, when $R^3$ and $R^4$ together with the atom they are attached form $C_{3-8}$ cycloalkyl, then the $C_{3-8}$ cycloalkyl is $C_3$ cycloalkyl, $C_4$ cycloalkyl, $C_5$ cycloalkyl, $C_6$ cycloalkyl, $C_7$ cycloalkyl, or $C_8$ cycloalkyl.

In a certain embodiment, when $R^3$ and $R^4$ are $C_{1-6}$ alkyl substituted with deuterium, then the $C_{1-6}$ alkyl is $C_{1-4}$ alkyl, or may be methyl, ethyl, n-propyl, isopropyl, n-butyl, isobutyl, sec-butyl or tert-butyl, or may be methyl.

In a certain embodiment, when $R^3$ and $R^4$ are $C_{1-6}$ alkyl substituted with deuterium, then the $C_{1-6}$ alkyl substituted with deuterium is $—CD_3$.

In a certain embodiment, Ar is

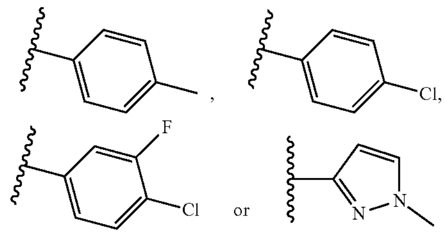

In a certain embodiment,

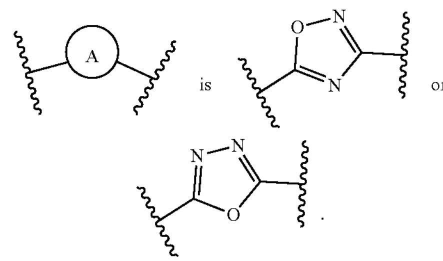

In a certain embodiment, when

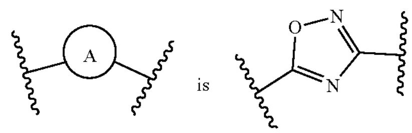

either side of

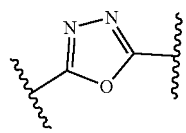 [SMILES: *c1nnc(*)o1]

can be attached to the Ar.

In a certain embodiment,

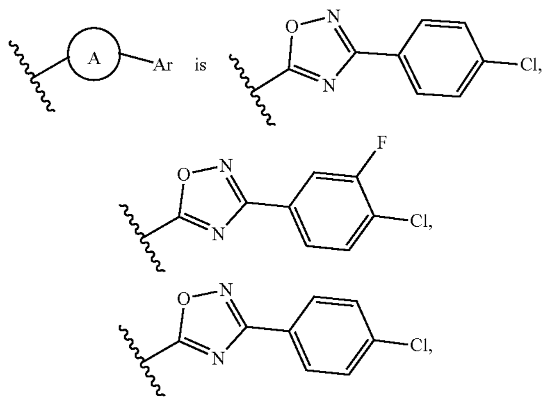

-continued
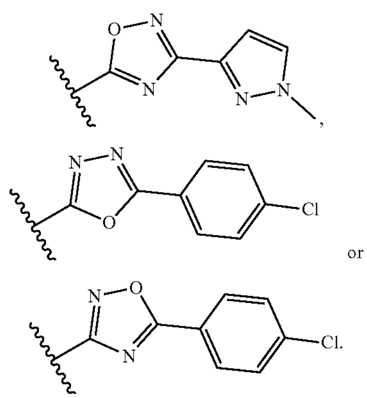
, or .
In a certain embodiment,
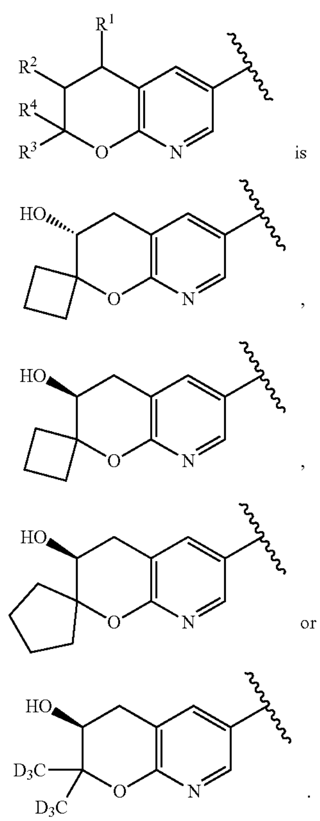
is , , or .
In a certain embodiment, the oxygen-containing heterocyclic compound of Formula I can have any one of the following structures:
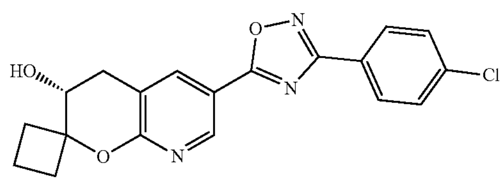
-continued
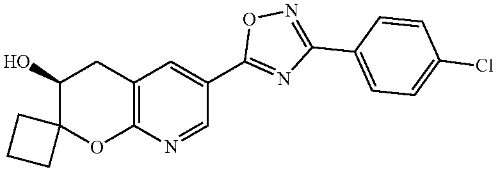
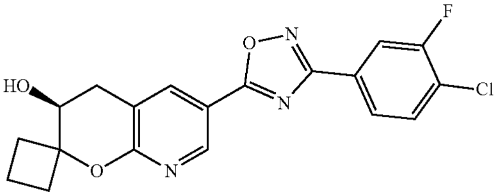
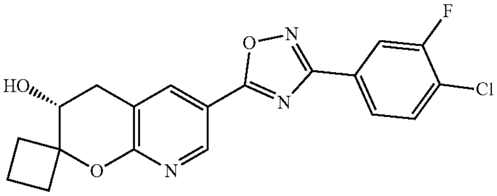
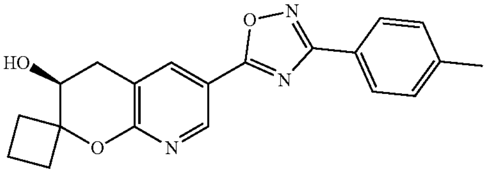
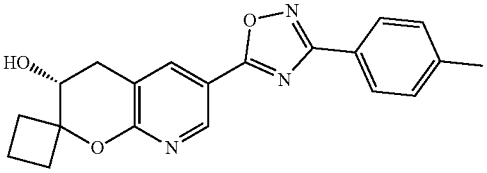
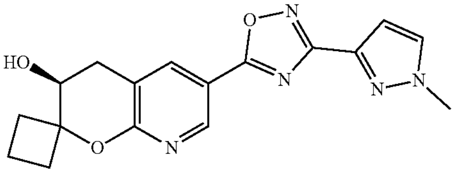
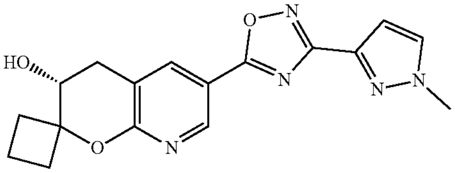
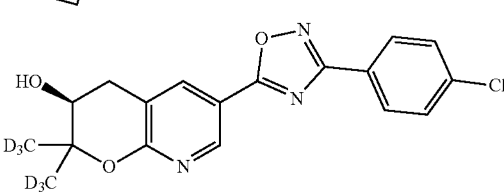
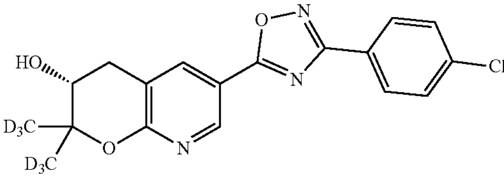

-continued

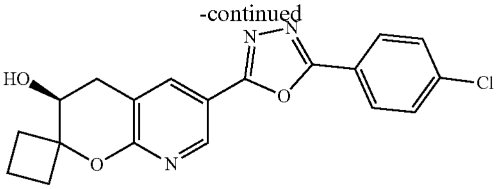

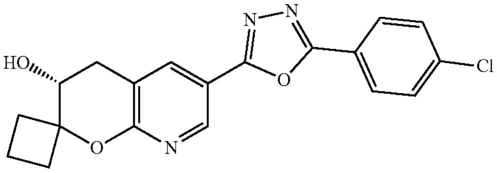

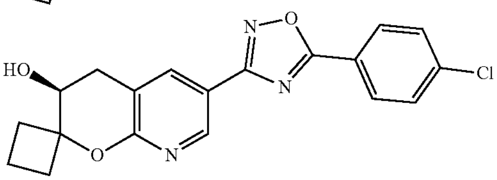

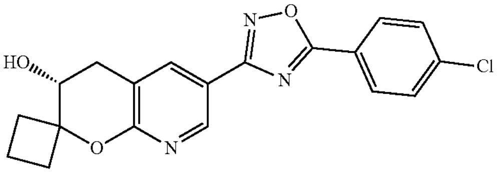

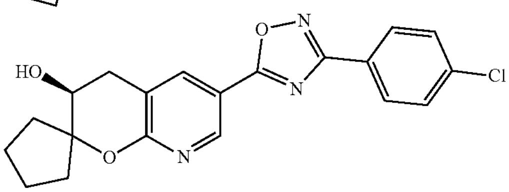

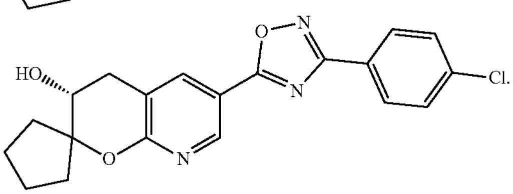

The present disclosure also provides a pharmaceutical composition comprising a substance A and a pharmaceutically acceptable excipient, wherein the substance A is a therapeutically effective amount of the oxygen-containing heterocyclic compound of Formula I, a pharmaceutically acceptable salt thereof, deuterated derivative thereof, a solvate thereof, a solvate of the pharmaceutically acceptable salt thereof or a crystal form thereof as described above.

In the present disclosure, the pharmaceutical composition can be in the form of an oral administration, as well as a sterile injectable aqueous solution, which can be prepared according to any known process for preparing pharmaceutical composition in the art.

The present disclosure also provides a method for inhibiting the interaction of homeodomain interacting protein kinase 2 with Smad3, said method comprising combining HIPK2 with a substance A, wherein the substance A is a therapeutically effective amount of the oxygen-containing heterocyclic compound of Formula I, a pharmaceutically acceptable salt thereof, deuterated derivative thereof, a solvate thereof, a solvate of the pharmaceutically acceptable salt thereof or a crystal form thereof as described above.

The present disclosure also provides a method for inhibiting Smad3 activation, wherein the method comprising bringing Smad3 into contact with a substance A, wherein the substance A is a therapeutically effective amount of the oxygen-containing heterocyclic compound of Formula I, a pharmaceutically acceptable salt thereof, deuterated derivative thereof, a solvate thereof, a solvate of the pharmaceutically acceptable salt thereof or a crystal form thereof as described above.

The present disclosure also provides a method for treating a fibrotic disease comprising administrating a substance A to a subject suffering from a fibrotic disease, wherein the substance A is a therapeutically effective amount of the oxygen-containing heterocyclic compound of Formula I, a pharmaceutically acceptable salt thereof, deuterated derivative thereof, a solvate thereof, a solvate of the pharmaceutically acceptable salt thereof or a crystal form thereof as described above, the disease is renal fibrosis, cardiac fibrosis, hepatic fibrosis, pulmonary fibrosis.

The term "pharmaceutically acceptable salt" refers to a salt of the compound disclosed herein which is prepared using relatively safe and pharmaceutically acceptable acids or bases. When the compound disclosed herein contains a relatively acidic functional group, a base addition salt can be obtained by contacting a neutral form of the compound with a sufficient amount of a pharmaceutically acceptable base in a pure solution or a suitable inert solvent. Pharmaceutically acceptable base addition salts include, but are not limited to: lithium salt, sodium salt, potassium salt, calcium salt, aluminum salt, magnesium salt, zinc salt, bismuth salt, ammonium salt, and diethanolamine salt. When the compound disclosed herein contains a relatively basic functional group, an acid addition salt can be obtained by contacting a neutral form of the compound with a sufficient amount of a pharmaceutically acceptable acid in a pure solution or a suitable inert solvent. The pharmaceutically acceptable acid includes inorganic acids, including, but not limited to: hydrochloric acid, hydrobromic acid, hydroiodic acid, nitric acid, carbonic acid, phosphoric acid, phosphorous acid, and sulfuric acid. The pharmaceutically acceptable acids include organic acids, including, but not limited to: acetic acid, propionic acid, oxalic acid, isobutyric acid, maleic acid, malonic acid, benzoic acid, succinic acid, suberic acid, fumaric acid, lactic acid, mandelic acid, phthalic acid, benzenesulfonic acid, p-toluenesulfonic acid, citric acid, salicylic acid, tartaric acid, methanesulfonic acid, isonicotinic acid, acidic citric acid, oleic acid, tannic acid, pantothenic acid, bitartrate, ascorbic acid, gentisic acid, fumaric acid, gluconic acid, saccharic acid, formic acid, ethanesulfonic acid, pamoic acid (i.e., 4,4'-methylene-bis(3-hydroxy-2-naphthoic acid)), and amino acids (e.g., glutamic acid and arginine). When a compound disclosed herein contains both relatively acidic functional group and relatively basic functional group, it can be converted to either base addition salt or acid addition salt. For details, see Berge et al., "Pharmaceutical Salts", Journal of Pharmaceutical Science 66:1-19 (1977), or Handbook of Pharmaceutical Salts: Properties, Selection, and Use (P. Heinrich Stahl and Camille G. Wermuth, ed., Wiley-VCH, 2002).

The term "halogen" refers to fluorine, chlorine, bromine or iodine.

The term "alkyl" refers to a linear or branched alkyl group having a specified number of carbon atoms. Examples of alkyl include methyl, ethyl, n-propyl, isopropyl, n-butyl, tert-butyl, isobutyl, sec-butyl, n-pentyl, n-hexyl, n-heptyl, n-octyl, and the like.

The terms "cycloalkyl" and "carbocyclic ring" refer to a saturated cyclic group consisting only of carbon atoms having a specified number of carbon atoms (e.g., $C_3$-$C_6$), which is a monocyclic, bridged or spiro ring. The cycloalkyl includes, but is not limited to, cyclopropyl, cyclobutyl, cyclopentyl, and cyclohexyl.

The term "heteroaryl" refers to a cyclic group having a specified number of ring atoms (e.g., 5-12 members), a specified number of heteroatoms (e.g., 1, 2, or 3) and specified heteroatom species (one or more of N, O and S), which is monocyclic or polycyclic, and has at least one aromatic ring (according to the Hückel's rule). Heteroaryls are linked to other fragments of the molecule through aromatic or non-aromatic rings. Heteroaryls include, but are not limited to, furyl, pyrrolyl, thienyl, pyrazolyl, imidazolyl, oxazolyl, thiazolyl, pyridinyl, pyrimidinyl, and indolyl.

The terms "heterocyclyl", "heterocycle" or "heterocycloalkyl" refer to a cyclic group having a specified number of ring atoms (e.g., 3-8 members), a specified number of heteroatoms (e.g., 1, 2, or 3) and specified heteroatom species (one or more of N, O and S), which is monocyclic, bridged, or spiro, and where each ring is saturated. Heterocycloalkyls include, but are not limited to, azetidinyl, tetrahydropyrrolyl, tetrahydrofuryl, morpholinyl, piperidinyl, and the like.

The term "hydroxyl" refers to a —OH group.

The term "cyano" refers to a —CN group.

EXPERIMENTAL SECTION

Example 1: The Synthesis Route of Compound 1

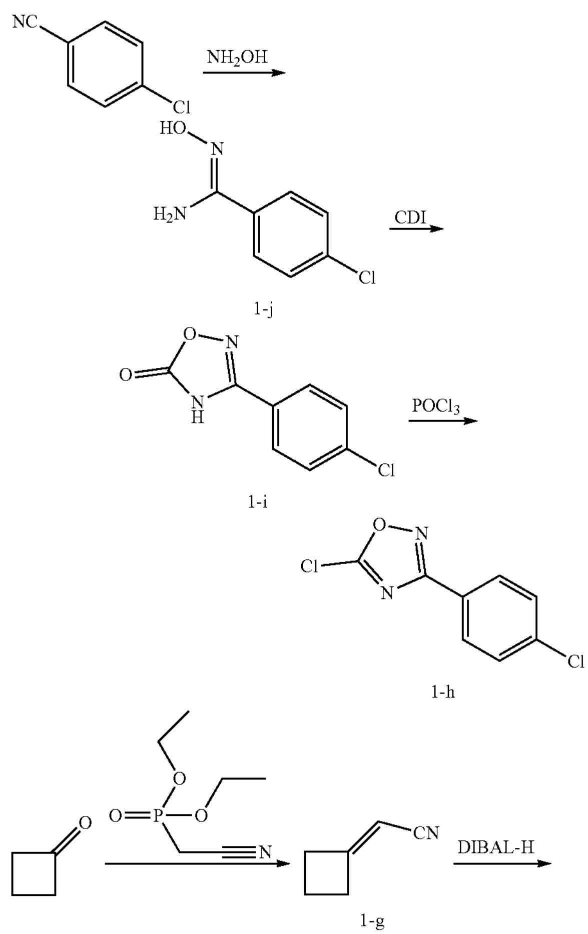

-continued

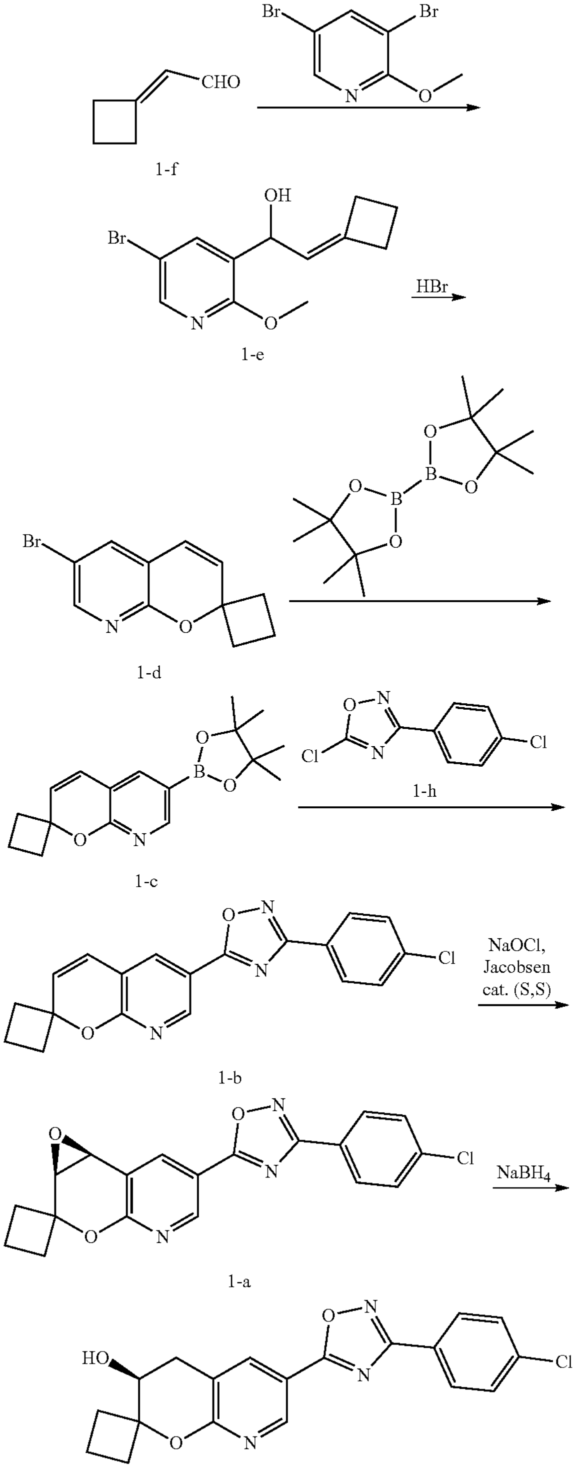

The Synthesis of Compound 1-j

To a mixture of 4-chlorobenzonitrile (11 g, 79.96 mmol) in EtOH (150 mL) was added hydroxylamine (21.13 g, 319.85 mmol). The mixture was stirred at 90° C. for 2 hours. After consumption of raw material (by LCMS), the mixture was concentrated in vacuo and the product was dried by lyophilization to obtained compound 1-j (13 g, crude).

The Synthesis of Compound 1-i

To a round bottom flask (100 mL) containing compound 1-j (700 mg, 4.10 mmol) was added 1,1-carbonyldiimidazole (CDI, 642.14 mg, 4.46 mmol) and 1,8-diazabicyclo [5.4.0]-7-undecene (DBU, 1.23 g, 4.87 mmol). Then 1,4-dioxane (10 mL) was sequentially added and the reaction mixture was stirred at 100° C. for 3 h. After cooling to ambient temperature, the mixture was diluted with water, and adjusted to pH ~2 with 3 M HCl in $H_2O$ and extracted with ethyl acetate (30 mL*2). The combined organic phases were washed with water, dried over anhydrous sodium sulfate, filtered and concentrated in vacuo, purified by silica column (EA:PE=0~15%) to obtain compound 1-i (400 mg, 50% yield).

The Synthesis of Compound 1-h

To a mixture of compound 1-i (1.0 g, 5.09 mmol) and $POCl_3$ (16.45 g, 105.90 mmol, 10 mL) was added 1,8-diazabicyclo[5.4.0]-7-undecene (DBU, 1.53 g, 10.05 mmol, 1.5 mL) at 0° C. The mixture was stirred at 100° C. for 12 hours. The mixture was poured into the ice water and the pH was adjusted to 9 by adding sat. $NaHCO_3$. The mixture was extracted with ethyl acetate (30 mL*3). The combined organic phases were washed with water, dried over anhydrous sodium sulfate, filtered and concentrated in vacuo, purified by silica column (EA:PE=0~10%) to give compound 1-h (455 mg, 42% yield).

The Synthesis of Compound 1-g

A mixture of diethyl cyanomethylphosphonate (51.43 g, 290.35 mmol), triethylamine (TEA, 26.65 g, 263.95 mmol) and lithium bromide (25.21 g, 290.35 mmol) in tetrahydrofuran (THF, 700 mL) was stirred at 25° C. for 2 h. After that, cyclobutanone (18.5 g, 263.95 mmol) was added to the mixture and some solid was separated out. Then the mixture was stirred at 25° C. for 12 h. TLC (EA (ethyl acetate):PE (Petroleum ether)=1:20, $KMnO_4$) showed that the raw material was consumed and new spot was detected. The reaction was diluted with water (500 ml) and extracted with ethyl acetate (500 mL*2). The organic layer was combined, washed with brine, dried over anhydrous sodium sulfate, filtered and concentrated in vacuo, purified by column (EA:PE=0~5%, 220 nm detected) to afford compound 1-g (10.6 g, 43% yield).

The Synthesis of Compound 1-f

To a solution of compound 1-g (10.6 g, 113.82 mmol) in dichloromethane (DCM, 200 mL) was slowly added 1.0 mol/L DIBAL-H in hexane (113.8 mL, 113.8 mmol) at −78° C. under $N_2$. After addition, the reaction was allowed to warm to 0° C. Then the reaction was stirred at 0° C. for 2.5 h under $N_2$. TLC (EA:PE=1:10, 254 nm) showed that the raw material was consumed. The reaction mixture was slowly poured into 1 M $H_2SO_4$ solution (200 mL) at 0° C. and stirred for 30 min. Then the organic layer was separated, and the aqueous phase was extracted with DCM (200 mL*2). The organic layer was combined, dried over anhydrous sodium sulfate, filtered and concentrated in vacuo at 25° C., purified by silica column (DCM:PE=0~20%) and afford compound 1-f (3.1 g, 28% yield).

The Synthesis of Compound 1-e

To a solution of compound 1-f (3.1 g, 32.25 mmol) and 3,5-dibromo-2-methoxypyridine (8.61 g, 32.25 mmol) in THF (100 mL) was slowly added 2.5 M n-BuLi solution in hexane (13.0 mL, 32.25 mmol) at −78° C. under $N_2$. Then the reaction mixture was stirred at this condition for 2.5 h. After consumption of raw material (by LCMS), the reaction was quenched with saturated $NH_4Cl$ (200 mL) and the mixture was extracted with ethyl acetate (200 mL*2). The organic layer was combined, washed with brined, dried over anhydrous sodium sulfate, filtered and concentrated in vacuo, purified by silica column (EA:PE=0~26%) and afford compound 1-e (3 g, 33% yield).

The Synthesis of Compound 1-d

To a mixture of compound 1-e (400 mg, 1.41 mmol) in glacial acetic acid (12 mL) was added 33% HBr/AcOH (0.8 mL, 4.94 mmol). Then the reaction was stirred at 80° C. for 3 h. After consumption of raw material (by LCMS), the reaction mixture was directly concentrated to move off the solvent, then to the residue was added saturated sodium carbonate (100 mL). The mixture was extracted with ethyl acetate (60 ml*2). The organic layer was combined, washed with brine, dried over anhydrous sodium sulfate, filtered and concentrated in vacuo, purified by silica column (EA: PE=0~50%) and afford compound 1-d (110 mg, 31% yield).

The Synthesis of Compound 1-c

To a mixture of 4,4,4',4',5,5,5',5'-octamethyl-2,2'-bi(1,3,2-dioxaborolane) (151 mg, 0.59 mmol), compound 1-d (100 mg, 0.40 mmol) and potassium acetate (117 mg, 1.2 mmol) in 1,4-dioxane (3 mL) added $Pd(dppf)Cl_2$ (28 mg, 0.04 mmol). After addition, the reaction mixture was bubbled with $N_2$ for 3 min and was stirred at 85° C. for 3 h. After consumption of raw material (by LCMS), the reaction mixture was concentrated and purified by silica column (EA:PE=0~20%) and afford compound 1-c (110 mg, 93% yield.

The Synthesis of Compound 1-b

To a mixture of compound 1-h (79 mg, 0.37 mmol), compound 1-c (110 mg, 0.37 mmol), sodium carbonate (120 mg, 1.11 mmol) in 1,4-dioxane (4 mL) and $H_2O$ (1 mL). was added $Pd(dppf)Cl_2$ (27 mg, 0.037 mmol). After addition, the reaction mixture was bubbled with $N_2$ for 3 min then was stirred at 95° C. for 3 h. After consumption of raw material (by LCMS), the reaction was diluted with water (20 mL) and extracted with ethyl acetate (20 mL*2). The organic layer was combined, washed with brine, dried over anhydrous sodium sulfate, filtered and concentrated in vacuo, purified by column (EA:PE=0~30%) to afford compound 1-b (51 mg, 39% yield).

The Synthesis of Compound 1-a

To a flask was added compound 1-b (51 mg, 0.15 mmol), (S,S)—[N,N'-Bis(3,5-di-tert-butylsalicylidene)-1,2-cyclohexanediamine]manganese(III) chloride (jacobsen cat (S,S)) (16 mg, 0.025 mmol) and $Na_2HPO_4$ solution (2.56 mg, 0.021 mmol) in $H_2O$ (0.4 mL) and DCM (2 mL), respectively. The reaction mixture was cooled to 0° C., and sodium hypochlorite (42 mg, 0.57 mmol) solution in $H_2O$ (1.03 mL) was slowly added to the mixture at this condition. After that, the reaction was stirred at 25° C. for 12 h. After consumption of raw material (by LCMS), the reaction was diluted with water (10 mL) and extracted with DCM (20 mL*2), the organic layer was combined, washed with brine, dried over anhydrous sodium sulfate, filtered and concentrated in vacuo, purified by silica column (EA:PE=0~30%) to afford compound 1-a (51 mg, 96% yield).

The Synthesis of Compound 1

To a solution of compound 1-a (51 mg, 0.14 mmol) in THF (1.5 mL) was added sodium borohydride (10.5 mg, 0.28 mmol) under $N_2$. Then the reaction mixture was stirred at 50° C. for 12 h under $N_2$. After consumption of raw material (by LCMS), The reaction was quenched with saturated $NH_4Cl$ (10 mL) and extracted with ethyl acetate (20 mL*2). The organic layer was combined, washed with brine, dried over anhydrous sodium sulfate, filtered and concentrated in vacuo, purified by silica column (EA: PE=0~40%) to afford compound 1 (13.3 mg, 26% yield). MS Found: 370.0 $[M+H]^+$; $^1H$ NMR (400 MHz, $CDCl_3$): δ

8.95 (d, J=2.2 Hz, 1H), 8.22-8.18 (m, 1H), 8.12-8.06 (m, 2H), 7.51-7.46 (m, 2H), 4.30-4.19 (m, 1H), 3.19 (dd, J=17.0, 4.0 Hz, 1H), 2.98 (dd, J=17.1, 3.8 Hz, 1H), 2.54-2.48 (m, 2H), 2.48-2.40 (m, 1H), 2.13-2.03 (m, 2H), 1.82-1.73 (m, 1H).

Example 2: The Synthesis Route of Compound 2

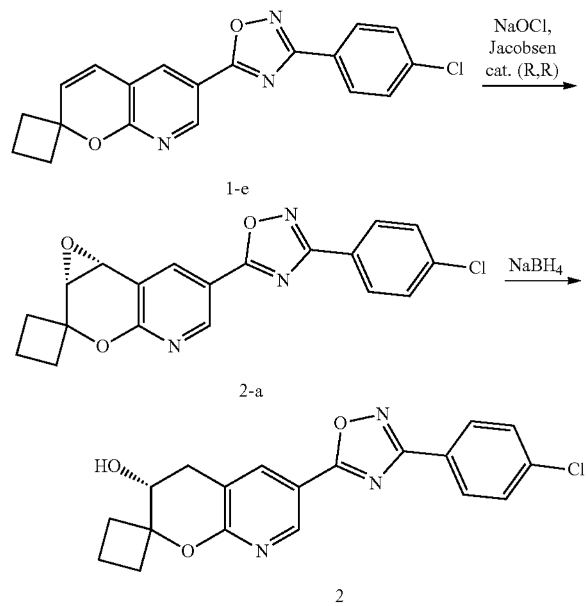

1-e 2-a

2

The Synthesis of Compound 2-a

To a mixture of 1-e (98 mg, 0.28 mmol), (R,R)—[N,N'-Bis(3,5-di-tert-butylsalicylidene)-1,2-cyclohexanediamine] manganese(III) chloride (jacobsen cat (R,R)) (31.7 mg, 0.05 mmol), $Na_2HPO_4$ (5.07 mg, 0.042 mmol) solution in $H_2O$ (0.4 mL) and DCM (4 mL) cooled to 0° C. was added the sodium hypochlorite (83.8 mg, 1.12 mmol) solution in $H_2O$ (2.04 mL). The reaction mixture was stirred at 25° C. for 12 h. After consumption of raw material (by LCMS), the reaction was diluted with water (20 mL) and extracted with DCM (30 mL*2), the organic layer was combined, washed with brine, dried over anhydrous sodium sulfate, filtered and concentrated in vacuo, purified by silica column (EA: PE=0~30%) to afford compound 2-a (65 mg, 63% yield).

The Synthesis of Compound 2

To a solution of compound 2-a (65 mg, 0.18 mmol) in THF (2 mL) was added sodium borohydride (13 mg, 0.35 mmol) under $N_2$. Then the reaction mixture was stirred at 50° C. for 12 h under $N_2$. After consumption of raw material (by LCMS), The reaction was quenched with saturated $NH_4Cl$ (10 mL) and the mixture was extracted with ethyl acetate (20 mL*2). The organic layer was combined, washed with brine, dried over anhydrous sodium sulfate, filtered and concentrated in vacuo, purified by silica column (EA: PE=0~40%) to afford compound 2 (9.01 mg, 14% yield). MS Found: 370.0 $[M+H]^+$; $^1H$ NMR (400 MHz, $CDCl_3$): δ 8.96 (d, J=2.3 Hz, 1H), 8.23-8.19 (m, 1H), 8.12-8.07 (m, 2H), 7.51-7.45 (m, 2H), 4.26 (dd, J=9.6 Hz, 4.0 Hz, 1H), 3.19 (dd, J=17.0 Hz, 4.1 Hz, 1H), 3.00-2.94 (m, 1H), 2.55-2.47 (m, 2H), 2.43 (dd, J=12.3, 8.6 Hz, 1H), 2.13-2.03 (m, 2H), 1.80-1.72 (m, 1H).

Example 3: The Synthesis Route of Compound 3

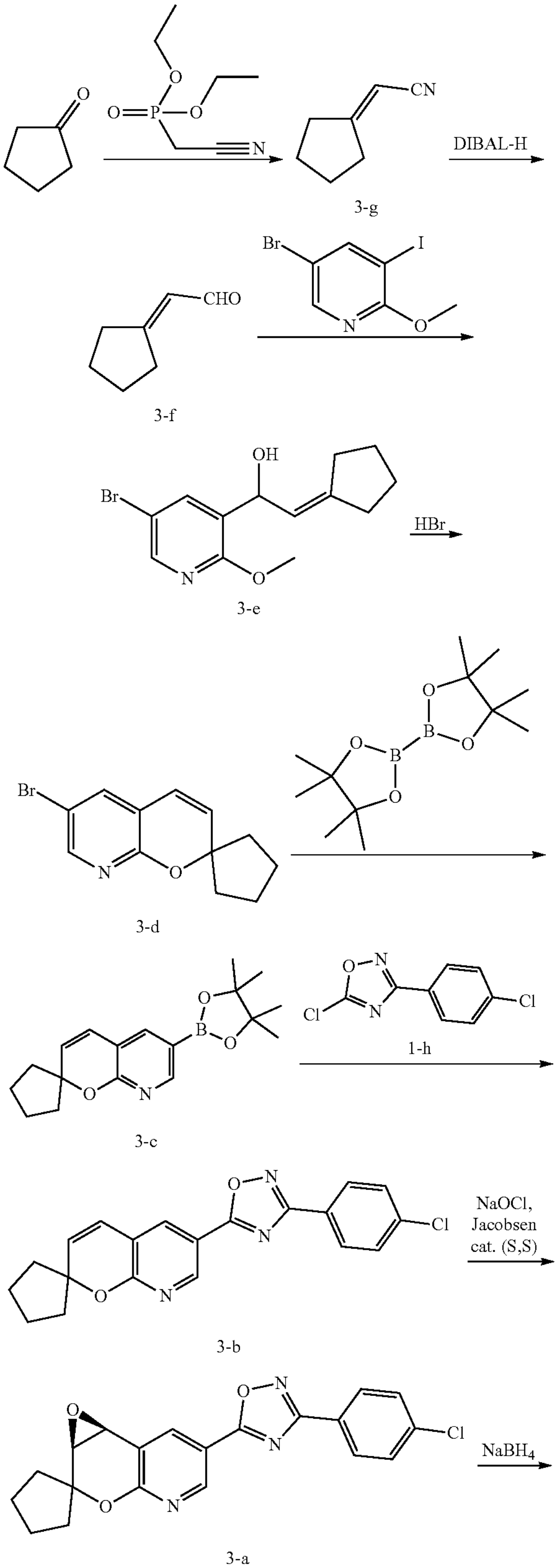

3-g 3-f 3-e 3-d 1-h 3-c 3-b 3-a

-continued

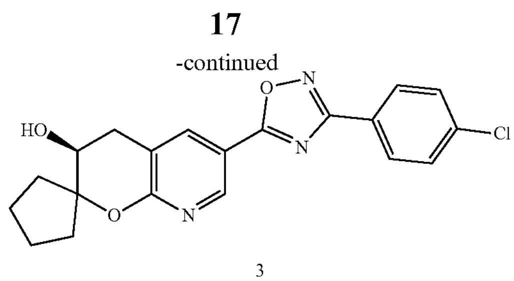

3

The Synthesis of Compound 3-g

A mixture of diethyl cyanomethylphosphonate (81.12 g, 457.94 mmol), TEA (46.29 g, 456.96 mmol) and lithium bromide (39.42 g, 458.33 mmol) in THF (400 mL) was stirred at 25° C. for 2 h. After that, cyclopentanone (35 g, 416.07 mmol) was added to the mixture and some solid was separated out. Then the mixture was stirred at 25° C. for 12 h. TLC (EA:PE=1:20, $KMnO_4$) showed that the raw material was consumed and new spot was detected. The reaction mixture was diluted with water (300 ml) and extracted with ethyl acetate (500 mL*2). The organic layer was combined, washed with brine, dried over anhydrous sodium sulfate, filtered and concentrated in vacuo, purified by silica column (EA:PE=0~5%, 220 nm detected) to afford compound 3-g (33 g, 74% yield). $^1H$ NMR (400 MHz, $CDCl_3$): δ 5.23-5.14 (m, 1H), 2.66-2.48 (m, 2H), 2.47-2.37 (m, 2H), 1.80-1.67 (m, 4H).

The Synthesis of Compound 3-f

To a solution of compound 3-g (33 g, 307.95 mmol) in DCM (300 mL) was slowly added 1.0 mol/L DIBAL-H in hexane (616.9 mL, 616.9 mmol) at −78° C. under $N_2$. After addition, the reaction mixture was allowed to warm to 0° C. and was stirred at 0° C. for 2.5 h under $N_2$. TLC (EA:PE=1:8, 254 nm) showed that the raw material was consumed. The reaction mixture was slowly poured into 1 M $H_2SO_4$ solution (600 mL) at 0° C. and stirred for 30 min. Then the organic layer was separated and the aqueous phase was extracted with DCM (300 mL*2). The organic layer was combined, dried over anhydrous sodium sulfate, filtered and concentrated in vacuo at 25° C., purified by silica column (DCM:PE=0~20%) to afford compound 3-f (13 g, 38% yield). $^1H$ NMR (400 MHz, $CDCl_3$): δ 9.77 (d, J=8.0 Hz, 1H), 6.02-5.87 (m, 1H), 2.73 (t, J=7.3 Hz, 2H), 2.47 (t, J=7.2 Hz, 2H), 1.82-1.72 (m, 2H), 1.66 (dd, J=13.8, 6.8 Hz, 2H).

The Synthesis of Compound 3-e

To a solution of 5-bromo-3-iodo-2-methoxypyridine (5 g, 15.93 mmol) THF (50 mL) was slowly added i-PrMgBr (2.8 M in 2-MeTHF (6.3 mL, 17.64 mmol) at 0° C. under $N_2$. The reaction mixture was stirred at 0° C. for 1 h. Then compound 3-f (2.11 g, 19.15 mmol) was added to the reaction mixture. Then the reaction mixture was stirred at this condition for 1 h. After consumption of raw material (by LCMS), the reaction was quenched with saturated $NH_4Cl$ (200 mL) and the mixture was extracted with ethyl acetate (200 mL*2). The organic layer was combined, washed with brine, dried over anhydrous sodium sulfate, filtered and concentrated in vacuo, purified by silica column (EA:PE=0~25%) to afford compound 3-e (1.1 g, 23% yield). $^1H$ NMR (400 MHz, $CDCl_3$): δ 8.10 (d, J=2.4 Hz, 1H), 7.75 (d, J=2.4 Hz, 1H), 5.44 (dd, J=5.4, 3.5 Hz, 2H), 3.97 (s, 3H), 2.53-2.39 (m, 2H), 2.31 (d, J=8.4 Hz, 3H), 1.77-1.65 (m, 3H).

The Synthesis of Compound 3-d

To a mixture of compound 3-e (1.1 g, 3.69 mmol) in glacial acetic acid (20 mL) was added 33% HBr/AcOH (2.1 mL, 12.92 mmol). Then the reaction was stirred at 80° C. for 3 h. After consumption of raw material (by LCMS), the reaction mixture was directly concentrated to move off the solvent. To the resulting residue was added saturated sodium carbonate (200 mL) and the mixture was extracted with ethyl acetate (50 ml*2), the organic layer was combined, washed with brine, dried over anhydrous sodium sulfate, filtered and concentrated in vacuo, purified by silica column (EA:PE=0~10%) to afford compound 3-d (84 mg, 8.5% yield). $^1H$ NMR (400 MHz, $CDCl_3$) δ 8.01 (d, J=2.4 Hz, 1H), 7.34 (d, J=2.4 Hz, 1H), 6.25 (d, J=9.8 Hz, 1H), 5.73 (d, J=9.8 Hz, 1H), 2.26-2.14 (m, 2H), 2.05-1.97 (m, 2H), 1.70 (t, J=4.7 Hz, 4H).

The Synthesis of Compound 3-c

To a mixture of 4,4,4',4',5,5,5',5'-octamethyl-2,2'-bi(1,3,2-dioxaborolane) (149 mg, 0.59 mmol), compound 3-d (103 mg, 0.39 mmol) and potassium acetate (116 mg, 1.2 mmol) in 1,4-dioxane (5 mL) was added $Pd(dppf)Cl_2$ (29 mg, 0.04 mmol). After addition, the reaction was bubbled with $N_2$ for 3 min. The reaction was stirred at 85° C. for 3 h. After consumption of raw material (by LCMS), the reaction was concentrated and purified by silica column (EA:PE=0~15%) to afford compound 3-c (150 mg, crude).

The Synthesis of Compound 3-b

To a mixture of compound 1-h (125 mg, 0.58 mmol), compound 3-c (150 mg, crude), sodium carbonate (132 mg, 0.96 mmol) in 1,4-dioxane (5 mL) and $H_2O$ (1 mL). was added $Pd(dppf)Cl_2$ (18 mg, 0.024 mmol) under $N_2$. After addition, the reaction was bubbled with $N_2$ for 3 min. The reaction was stirred at 100° C. for 3 h. After consumption of raw material (by LCMS), the reaction was diluted with water (20 mL) and extracted with ethyl acetate (30 mL*2). The organic layer was combined, washed with brine, dried over anhydrous sodium sulfate, filtered and concentrated in vacuo, purified by silica column (EA:PE=0~30%) to afford compound 3-b (72 mg, 51% yield).

The Synthesis of Compound 3-a

To a mixture of compound 3-b (72 mg, 0.20 mmol), (S,S)—[N,N'-Bis(3,5-di-tert-butylsalicylidene)-1,2-cyclohexanediamine]manganese(III) chloride (jacobsen cat (S,S)) (19 mg, 0.03 mmol), $Na_2HPO_4$ (4.3 mg, 0.03 mmol) solution in $H_2O$ (0.5 mL) and DCM (5 mL) cooled to 0° C. was added sodium hypochlorite (60 mg, 0.8 mmol) solution in $H_2O$ (1 mL) slowly. After that, the reaction was stirred at 25° C. for 12 h. After consumption of raw material (by LCMS), the reaction mixture was diluted with water (10 mL) and extracted with DCM (20 mL*2), the organic layer was combined, washed with brine, dried over anhydrous sodium sulfate, filtered and concentrated in vacuo, purified by silica column (EA:PE=0~30%) to afford compound 3-a (42 mg, 56% yield).

The Synthesis of Compound 3

To a mixture of compound 3-a (42 mg, 0.11 mmol) in THF (3 mL) was added sodium borohydride (13 mg, 0.33 mmol) under $N_2$. Then the reaction was stirred at 50° C. for 12 h under $N_2$. After consumption of raw material (by LCMS), The reaction was quenched with saturated $NH_4Cl$ (10 mL) and the mixture was extracted with ethyl acetate (20 mL*2). The organic layer was combined, washed with brine, d dried over anhydrous sodium sulfate, filtered and concentrated in vacuo, purified by Prep-HPLC to afford compound 3 (3.01 mg, 7.1% yield). MS found 384.1 $[M+1]^+$; $^1H$ NMR (400 MHz, $CDCl_3$): δ 8.90 (s, 1H), 8.14 (d, J=51.1 Hz, 3H), 7.47 (s, 2H), 4.02 (s, 1H), 3.16 (d, J=15.3 Hz, 1H), 2.98 (d, J=15.4 Hz, 1H), 2.29 (s, 1H), 2.05 (d, J=38.5 Hz, 4H), 1.77 (s, 3H).

Example 4: The Synthesis Route of Compound 4

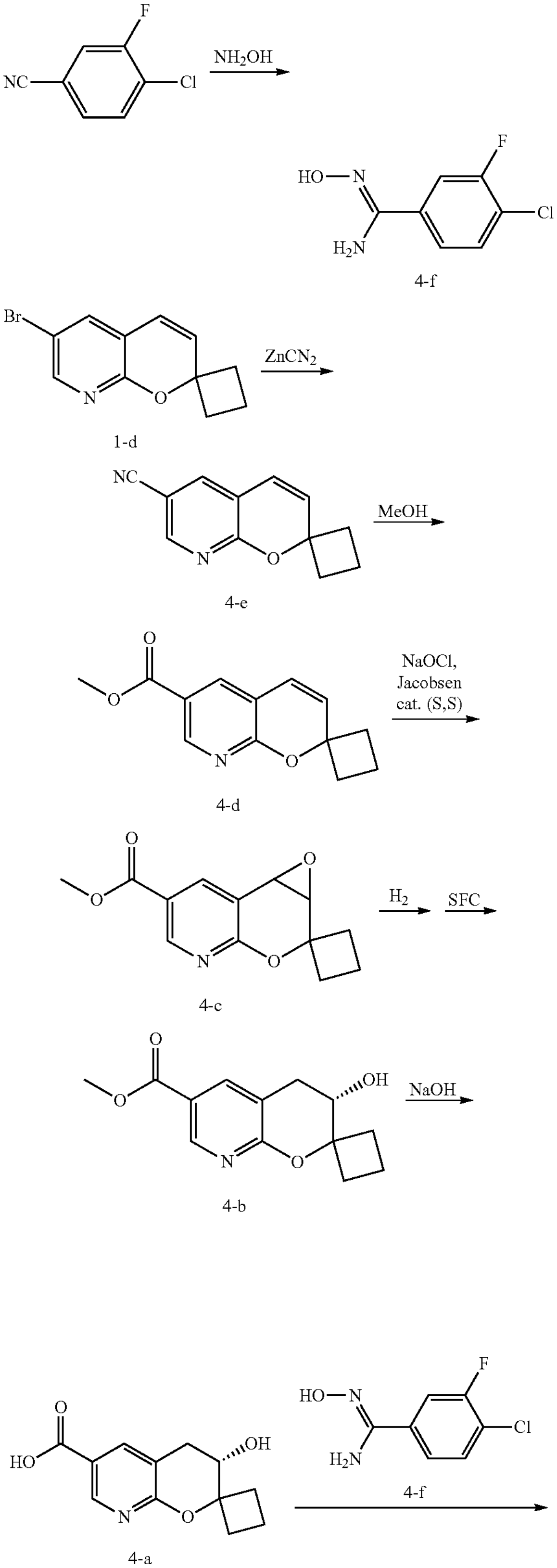

-continued

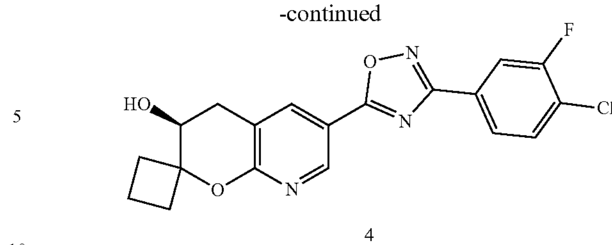

4

The Synthesis of Compound 4-f

To a mixture of 4-chloro-3-fluorobenzonitrile (311 mg, 2 mmol) in EtOH (10 mL) was added 50% aqueous $NH_2OH$ (528 mg, 8 mmol). The mixture was stirred at 90° C. for 1 hours. Then LCMS showed that the desired product was formed. The mixture was concentrated in vacuo to give compound 4-f (350 mg, 93% yield).

The Synthesis of Compound 4-e

A mixture of 1-d (7.7 g, 30.54 mmol), $Zn(CN)_2$ (14.3 g, 112.16 mmol), 2-Dicyclohexylphosphino-2',6'-dimethoxybiphenyl (S-Phos, 2.5 g, 6.11 mmol), $Pd_2(dba)_3$ (5.6 g, 6.11 mmol) in DMF (200 mL) was heated to 100° C. in a microwave reactor for 1 h. Saturated aqueous $NH_4Cl$ (50 mL) was added, and the mixture was partitioned between water (100 mL) and DCM (100 mL), and the layers were separated. The organic layer was washed with brine (20 mL), dried ($MgSO_4$), filtered, and concentrated under reduced pressure. The crude product was purified by flash chromatography, eluting with 0-25% EtOAc/hexanes, to give compound 4-e (4.3 g, 71% yield).

The Synthesis of Compound 4-d

To a solution of compound 4-e (3 g, 15.13 mmol) in MeOH (80 mL) was slowly added concentrated $H_2SO_4$ (20 mL) at 0° C. After addition, the reaction was stirred at 80° C. for 24 h. The solution was cooled to room temperature and concentrated under reduced pressure. Then DCM (100 mL) and NaOH (2 M) was added to adjust pH to 7-8, and the layers were separated. The aqueous layer was treated with DCM (50 mL), and the combined organic phases were dried ($MgSO_4$), filtered, and concentrated under reduced pressure. The crude product was purified by flash chromatography, eluting with 0-25% EtOAc/hexanes, to give compound 4-d (2.4 g, 69% yield).

The Synthesis of Compound 4-c

To a mixture of compound 4-d (1.5 g, 6.49 mmol), (S,S)—[N,N'-Bis(3,5-di-tert-butylsalicylidene)-1,2-cyclohexanediamine]manganese(III) chloride (jacobsen cat (S,S)) (0.72 g, 1.13 mmol) and $Na_2HPO_4$ (0.12 g, 0.85 mmol) solution in $H_2O$ (18 mL) and DCM (80 mL) cooled to 0° C. was added sodium hypochlorite (1.93 g, 25.96 mmol) solution in $H_2O$ (46 mL) slowly. After that, the reaction was stirred at rt (25° C.) for 12 h. After consumption of raw material (by LCMS), the reaction was diluted with water (50 mL) and extracted with DCM (50 mL*2), the organic layer was combined, washed with brine, dried over anhydrous sodium sulfate, filtered and concentrated in vacuo, purified by silica column (EA:PE=0~30%) to afford compound 4-c (850 mg, 53% yield).

The Synthesis of Compound 4-b

To a mixture of compound 4-c (850 mg, 3.44 mmol) in MeOH (20 mL) was added wet 10% Pd/C (250 mg). The mixture was purged by $H_2$ for 2 times. Then the mixture was stirred at rt (25° C.) for 12 h. The mixture was filtered and the filter cake was washed by MeOH (50 mL*2). The filtration was concentrated in vacuo to afford crude compound (830 mg) which was dissolved in MeOH (35 mL) and purified by supercritical fluid chromatography (SFC). The eluent was concentrated in vacuo and the residue was dried to give compound 4-b (430 mg, 50% yield).

The Synthesis of Compound 4-a

To a mixture of compound 4-b (430 mg, 1.73 mmol) in MeOH (20 mL) and $H_2O$ (8 mL) was added sodium hydroxide (138 mg, 3.46 mmol). The mixture was stirred at 25° C. for 12 hours. The solution was concentrated under reduced pressure and diluted with $H_2O$ (8 mL). The pH of the mixture was adjusted with HCl (2 M) to 6. The mixture was dried by lyophilization. 600 mg of compound 4-a was obtained. Some NaCl was remained in it. The product would be used to next step reaction without any purification.

The Synthesis of Compound 4

To a mixture of compound 4-a (100 mg, 0.43 mmol) in DMF (2 mL) was added CDI (139 mg, 0.86 mmol). The mixture was stirred at 25° C. for 1 hour. Then 4-f (121 mg, 0.64 mmol) was added to the above mixture and the mixture was stirred at 120° C. for 12 hours. The mixture purified by Prep-HPLC to afford compound 4 (21.07 mg, 13% yield). MS found 388.1[M+1]$^+$; $^1$H NMR (400 MHz, $CDCl_3$): δ 8.87 (d, J=1.9 Hz, 1H), 8.13 (s, 1H), 7.92-7.79 (m, 2H), 7.53-7.44 (m, 1H), 4.19 (t, J=3.9 Hz, 1H), 3.12 (dd, J=17.0, 3.9 Hz, 1H), 2.96-2.89 (m, 1H), 2.45 (dd, J=10.5, 6.6 Hz, 2H), 2.41-2.33 (m, 1H), 2.07-1.93 (m, 2H), 1.78-1.65 (m, 1H).

Example 5: The Synthesis Route of Compound 5

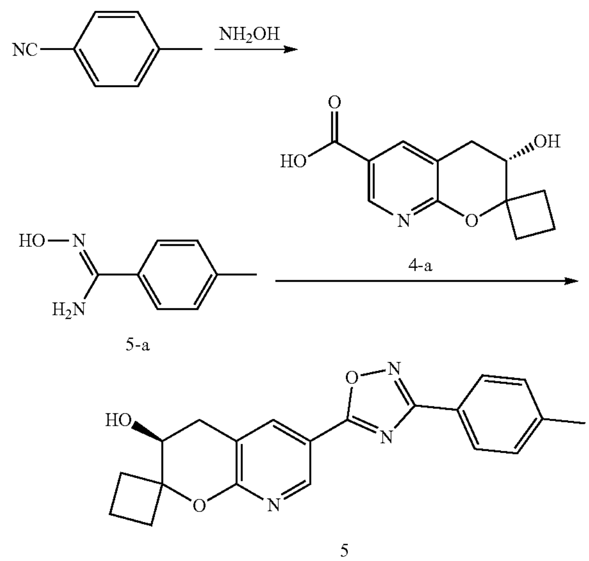

5-a 4-a

5

The Synthesis of Compound 5-a

To a mixture of 4-methylbenzonitrile (500 mg, 4.27 mmol) in EtOH (10 mL) was added 50% aqueous $NH_2OH$ (1.13 g, 17.08 mmol). The mixture was stirred at 90° C. for 1 hours. Then LCMS showed that the desired product was formed. The mixture was concentrated in vacuo to give compound 5-a (520 mg, 81% yield).

The Synthesis of Compound 5

To a solution of compound 4-a (125 mg, 0.53 mmol) in DMF (3 mL) was added CDI (172 mg, 1.06 mmol). The mixture was stirred at 25° C. for 1 hour. Then compound 5-a (120 mg, 0.8 mmol) was added to the above mixture and stirred at 120° C. for 3 hours. LCMS showed that the desired product was generated. The mixture was extracted with EtOAc (80 mL*3). The organic layers were concentrated in vacuo. The product was purified by Prep-HPLC to afford compound 5 (9.75 mg, 5.3% yield). MS found 350.1 [M+1]$^+$; $^1$H NMR (400 MHz, $CDCl_3$): δ 8.91 (d, J=1.8 Hz, 1H), 8.19 (s, 1H), 8.01 (d, J=8.1 Hz, 2H), 7.29 (d, J=8.0 Hz, 2H), 4.24 (t, J=3.8 Hz, 1H), 3.17 (dd, J=17.0, 3.8 Hz, 1H), 2.97 (dd, J=17.0, 3.7 Hz, 1H), 2.50 (t, J=8.3 Hz, 2H), 2.42 (s, 3H), 2.13-2.02 (m, 2H), 1.82-1.70 (m, 2H).

Example 6: The Synthesis Route of Compound 6

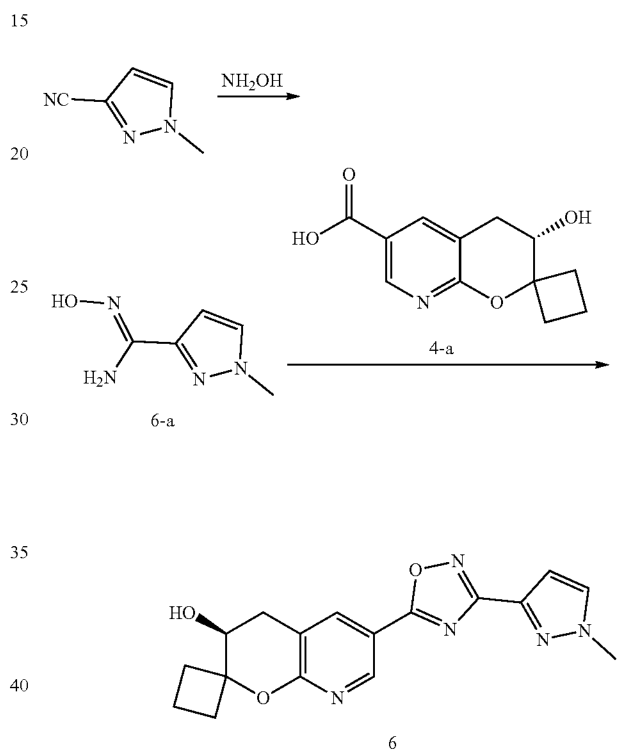

4-a 6-a

6

The Synthesis of Compound 6-a

To a mixture of 1-methyl-1H-pyrazole-3-carbonitrile (100 mg, 0.93 mmol) in EtOH (5 mL) was added 50% aqueous $NH_2OH$ (246 mg, 3.72 mmol). The mixture was stirred at 90° C. for 1 hours. Then LCMS showed that the desired product was formed. The mixture was concentrated in vacuo to give compound 6-a (130 mg, 99% yield).

The Synthesis of Compound 6

To a mixture of compound 4-a (146 mg, 0.62 mmol) in DMF (3 mL) was added CDI (201 mg, 1.24 mmol). The mixture was stirred at 25° C. for 1 hour. Then 6-a (140 mg, 0.93 mmol) was added to the above mixture and stirred at 120° C. for 3 hours. LCMS showed that the desired product was generated. The product was purified by purified by prep-HPLC to afford compound 6 (46.17 mg, 22% yield). MS found 340.1 [M+1]$^+$; $^1$H NMR (400 MHz, $CDCl_3$): δ 8.98 (d, J=2.0 Hz, 1H), 8.26 (d, J=1.0 Hz, 1H), 7.46 (d, J=2.2 Hz, 1H), 6.87 (d, J=2.3 Hz, 1H), 4.22 (t, J=3.9 Hz, 1H), 4.02 (s, 3H), 3.14 (dd, J=17.0, 4.0 Hz, 1H), 2.93 (dd, J=17.1, 3.9 Hz, 1H), 2.57-2.31 (m, 3H), 2.03 (ddd, J=14.6, 10.4, 5.8 Hz, 3H), 1.84-1.63 (m, 1H).

Example 7: The Synthesis Route of Compound 7

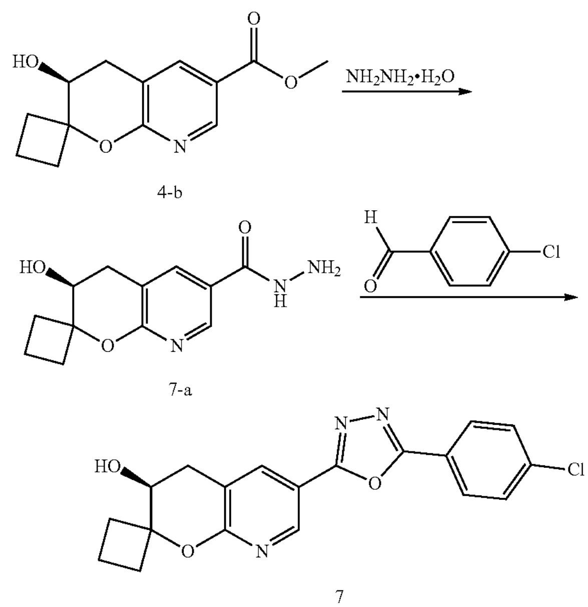

4-b 7-a

7

The Synthesis of Compound 7-a

To a solution of compound 4-b (150 mg, 0.60 mmol) in EtOH (10 mL) was added hydrazine monohydrate (2 mL). The mixture was stirred at 90° C. for 12 h. The solvents were removed in vacuo and to the crude product was triturated with PE to give compound 7-a (140 mg, 93% yield).

The Synthesis of Compound 7

To a solution of compound 7-a (140 mg, 0.56 mmol) in DCM (20 mL) was added 4-chlorobenzaldehyde (79 mg, 0.56 mmol) and ceric ammonium nitrate (307 mg, 0.56 mmol). The mixture was stirred at 40° C. for 12 h. The mixture purified by Prep-HPLC to afford compound 7 (6.15 mg, 3% yield) as white solid. MS found 370.0 $[M+1]^+$; $^1H$ NMR (400 MHz, $CDCl_3$): δ 8.75 (d, J=2.2 Hz, 1H), 8.15-8.07 (m, 1H), 8.05-7.96 (m, 2H), 7.48-7.41 (m, 2H), 4.18 (t, J=3.9 Hz, 1H), 3.11 (dd, J=17.1, 4.0 Hz, 1H), 2.90 (dd, J=17.2, 3.9 Hz, 1H), 2.44 (t, J=8.5 Hz, 2H), 2.38-2.32 (m, 1H), 2.08-1.99 (m, 2H), 1.77 (d, J=9.1 Hz, 1H).

Example 8: The Synthesis Route of Compound 8

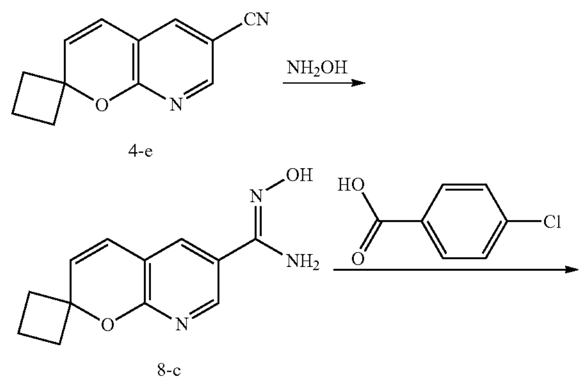

4-e 8-c

-continued

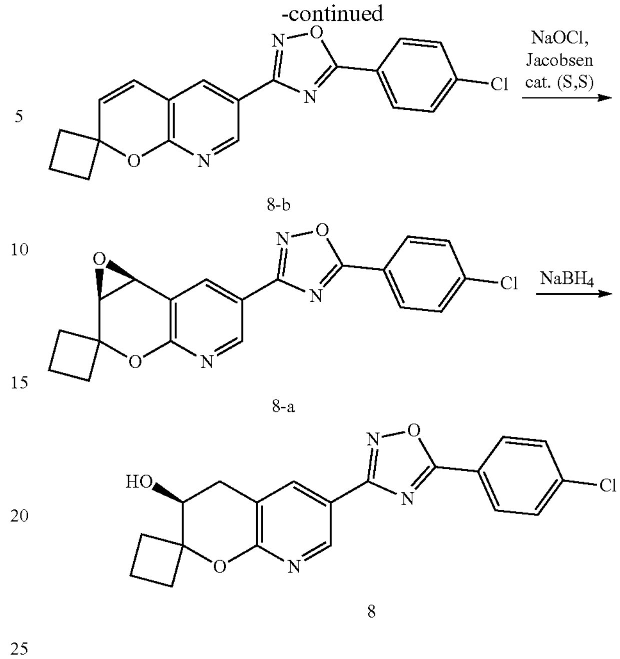

8-b 8-a

8

The Synthesis of Compound 8-c

To a mixture of compound 4-e (120 mg, 0.61 mmol) in EtOH (5 mL) was added 50% aq. $NH_2OH$ (161 mg, 2.44 mmol). The mixture was stirred at 90° C. for 1 hour. Then LCMS showed that the desired product was formed. The mixture was concentrated in vacuo to give compound 8-c (130 mg, 93% yield).

The Synthesis of Compound 8-b

To a mixture of 4-chlorobenzoic acid (58 mg, 0.37 mmol) in DMF (3 mL) was added CDI (120 mg, 0.74 mmol). The mixture was stirred at 25° C. for 1 hour. Then compound 8-c (130 mg, 0.56 mmol) was added and the mixture was stirred at 120° C. for 3 hours. LCMS showed that the desired product was generated. After consumption of raw material (by LCMS), the reaction mixture was diluted with water (10 mL) and extracted with ethyl acetate (20 mL*2). The organic layer was combined, washed with brine, dried over anhydrous sodium sulfate, filtered and concentrated in vacuo, purified by silica column (EA:PE=0~20%) to afford compound 8-b (30 mg, 23% yield).

The Synthesis of Compound 8-a

To a mixture of compound 8-b (30 mg, 0.085 mmol), (S,S)—[N,N'-Bis(3,5-di-tert-butylsalicylidene)-1,2-cyclohexanediamine]manganese(III) chloride (jacobsen cat) (S,S) (8.3 mg, 0.013 mmol), $Na_2HPO_4$ (1.7 mg, 0.012 mmol) solution in $H_2O$ (0.2 mL) and DCM (2 mL) cooled to 0° C. was added sodium hypochlorite (25 mg, 0.34 mmol) solution in $H_2O$ (0.5 mL) slowly. After that, the reaction was stirred at 25° C. for 12 h. After consumption of raw material (by LCMS), the reaction was diluted with water (10 mL) and extracted with DCM (20 mL*2). The organic layer was combined, washed with brine, dried over anhydrous sodium sulfate, filtered and concentrated in vacuo, purified by silica column (EA:PE=0~30%) to afford compound 8-a (27 mg, 86% yield).

The Synthesis of Compound 8

To a mixture of compound 8-a (28 mg, 0.076 mmol) in THF (2 mL) was added sodium borohydride (5.76 mg, 0.152 mmol) under $N_2$. Then the reaction was stirred at 50° C. for 12 h under $N_2$. After consumption of raw material (by LCMS), The reaction was quenched with saturated $NH_4Cl$ (10 mL) and the mixture was extracted with ethyl acetate (20 mL*2). The organic layer was combined, washed with brine, dried over anhydrous sodium sulfate, filtered and concentrated in vacuo, purified by silica column (EA:PE=0~40%) to afford compound 8 (2.57 mg, 9.1% yield). MS Found: 370.0 $[M+H]^+$; $^1H$ NMR (400 MHz, $CDCl_3$): δ 8.90 (d, J=2.1 Hz, 1H), 8.20-8.11 (m, 3H), 7.54 (d, J=8.6 Hz, 2H), 4.23 (t, J=3.8 Hz, 1H), 3.18 (dd, J=17.0, 4.1 Hz, 1H), 2.96 (dd, J=17.1, 3.8 Hz, 1H), 2.49 (dd, J=15.6, 6.9 Hz, 2H), 2.44-2.37 (m, 1H), 2.13-2.03 (m, 2H), 1.80-1.72 (m, 1H).

Example 9: The Synthesis Route of Compound 9

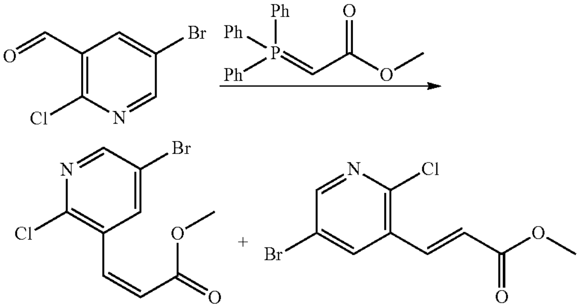

9-f-1 9-f-2

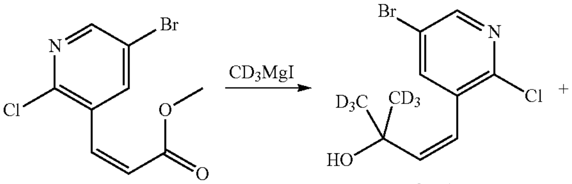

9-f-1 9-e-1

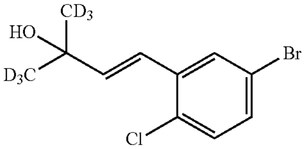

9-e-2

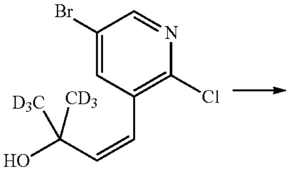

9-e-1

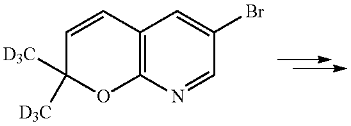

9-d

-continued

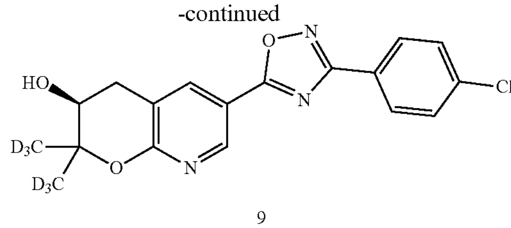

9

The Synthesis of Compound 9-f-1

A mixture of 5-bromo-2-chloronicotinaldehyde (1.00 g, 4.54 mmol), Methyl (Triphenylphosphoranylidene)acetate (1.82 g, 5.44 mmol) and THF (20 mL) was stirred at 80° C. for 2 hours under $N_2$. The reaction mixture was cooled to room temperature, concentrated. The resulting residue was purified by flash chromatography (PE/EA=2:1), to afford compound 94-1 (190 mg, 15% yield) as white solid, and compound 9-f-2 (877 mg, 70% yield) as white solid. compound 94-1: LC-MS (ESI): m/z=275.9 $[M+1]^+$; compound 9-f-2: MS Found: 275.9 $[M+1]^+$.

The Synthesis of Compound 9-e-1

To a solution of compound 94-1 (190 mg, 0.69 mmoL) in THF (10 mL) cooled to 0° C. was slowly added $CD_3MgI$ solution (2.06 mL, 2.06 mmoL, 1 M) in ethyl ether under $N_2$. After addition, the mixture was stirred at 0° C. for 2 hours. The reaction was quenched with saturated $NH_4Cl$ (30 mL) and the mixture was extracted with ethyl acetate (50 mL*2). The combined organic phases were dried over anhydrous sodium sulfate, filtered and concentrated in vacuo, purified by flash chromatography (PE/EA=2:1) to afford compound 9-e-1 (120 mg, 62% yield) as white solid. MS Found: 281.9 $[M+H]^+$.

The Synthesis of Compound 9-d

To a solution of compound 9-e-1 (10 mg, 0.035 mmoL) in N,N-Dimethylacetamide (2 mL) at room temperature was added cesium carbonate (23 mg, 0.071 mmoL). The mixture was stirred at 80° C. overnight. The reaction mixture was cooled to room temperature and $H_2O$ (10 mL) was added. The mixture was extracted with ethyl acetate (25 mL*2) and the combined organic phases were washed with sat. $NH_4Cl$ (50 mL*3), dried over anhydrous sodium sulfate, filtered and concentrated in vacuo, purified by flash chromatography (PE/EA=2:1), to afford compound 9-d (6 mg, 69%) as white solid. MS Found: 246.0 $[M+H]^+$.

The Synthesis of Compound 9

According to Example 1, compound 9-d was used to replace compound 1-d to obtain compound 9. MS Found: 364.1 $[M+H]^+$.

Other examples not specifically described above were made analogously.

For the data in Table 1, the Bight-Glo™ Luciferase Assay System from Promega was used with TGF/SMAD Signaling Pathway SBE Reporter-HEK293 Cell Line from BPSbioscience. On day 1 SBE reporter-HEK293 cells were seeded at a density of 25,000 cells per well into a white clear-bottom 96-well microplate in 100 μL of growth medium without geneticin. The plate was incubated at 37° C. in a $CO_2$ incubator for 24 hrs. The wells were renewed with 60 μL assay medium and treated with test compounds by adding 5 μL of compounds in medium. The concentration of test compound in medium is adjusted so that 5 μL will provide the desired molarity of the solution. After 4 hours, TGFβ was added to 10 ng/mL. The plate was incubated at 37° C. in a $CO_2$ incubator overnight (18 hours). One hour prior to assay all medium was replaced. The luciferase assay was run using ONE-Step™ Luciferase Assay System by adding 100 μL of ONE-Step™ Luciferase reagent per well, rocking at room temperature for ~15 to 30 minutes and measuring luminescence using a luminometer. The signals were normalized to percentage inhibition, with non-TGF treated cells as 100% inhibition, and the data were processed by Graphpad Prism.

Test results in the luciferase screen are shown in Table 1. The symbol "*" indicates $IC_{50}$<100 nM, "" indicates $IC_{50}$≥100 nM but <10 μM, "*" indicates $IC_{50}$≥10 μM.

TABLE 1

| Compound | Luciferase $IC_{50}$ (nM) |
|---|---|
| 1 | ** |
| 2 | *** |
| 3 | * |
| 4 | * |
| 5 | * |
| 6 | * |
| 7 | ** |
| 8 | * |
| 9 | *** |

While typical embodiments have been set forth for the purpose of illustration, the foregoing descriptions and examples should not be deemed to be a limitation on the scope of the invention. Accordingly, various modifications, adaptations, and alternatives may occur to one skilled in the art without departing from the spirit and scope of the present invention.

What is claimed is:

1. An oxygen-containing heterocyclic compound represented by Formula I, a pharmaceutically acceptable salt thereof, deuterated derivative thereof, a solvate thereof, a solvate of the pharmaceutically acceptable salt thereof or a crystal form thereof:

I

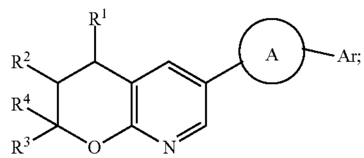

wherein:

Ar is $C_{6-20}$ aryl, $C_{6-20}$ aryl substituted with one or more $R^{1-1}$, "5-12 membered heteroaryl containing 1-4 heteroatoms selected from O, S and N", or "5-12 membered heteroaryl containing 1-4 heteroatoms selected from O, S and N" substituted with one or more $R^{1-2}$;

$R^{1-1}$ and $R^{1-2}$ are independently selected from halogen, hydroxyl and $C_{1-6}$ alkyl;

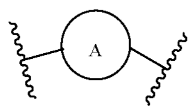

is a 5-6 membered heteroaryl containing 1-3 heteroatoms selected from O, S and N;

$R^1$ and $R^2$ are independently selected from hydrogen, deuterium, hydroxyl, $C_{1-6}$ alkyl, amino, and —$OC^{1-6}$ alkyl;

$R^3$ and $R^4$ are $C_{1-6}$ alkyl substituted with deuterium, or, $R^3$ and $R^4$ together with the atom they are attached form $C_{3-8}$ cycloalkyl, $C_{3-8}$ cycloalkyl substituted with $R^{1-3}$, 4- to 10-membered heterocycloalkyl containing 1-3 heteroatoms selected from O, S and N, "4- to 10-membered heterocycloalkyl containing 1-3 heteroatoms selected from O, S and N" substituted with $R^{1-4}$, and $R^{1-3}$ and $R^{1-4}$ are independently selected from halogen, deuterium, hydroxyl and $C_{1-6}$ alkyl.

2. The oxygen-containing heterocyclic compound represented by Formula I, the pharmaceutically acceptable salt thereof, deuterated derivative thereof, a solvate thereof, a solvate of the pharmaceutically acceptable salt thereof or a crystal form thereof according to claim 1, the oxygen-containing heterocyclic compound represented by Formula I has the structure of Formula II:

II

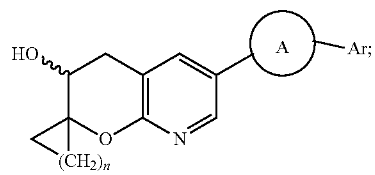

wherein represents , or a mixture of and ;

n is 1, 2, 3, 4 or 5; and

Ar and

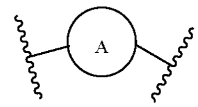

are defined as in the Formula I.

3. The oxygen-containing heterocyclic compound represented by Formula II, the pharmaceutically acceptable salt thereof, deuterated derivative thereof, a solvate thereof, a solvate of the pharmaceutically acceptable salt thereof or a crystal form thereof according to claim 2, wherein, Ar is $C_{6-20}$ aryl substituted with one or more $R^{1-1}$, or "5-12 membered heteroaryl containing 1-4 heteroatoms independently selected from O, S and N" substituted with one or more $R^{1-2}$;

$R^{1-1}$ and $R^{1-2}$ are independently selected from halogen and $C_{1-6}$ alkyl;

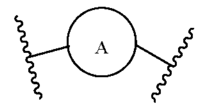

is a 5-6 membered heteroaryl containing 1-3 heteroatoms independently selected from O, S and N;

represents or ; and n is 2 or 3.

4. The oxygen-containing heterocyclic compound represented by Formula I, the pharmaceutically acceptable salt thereof, deuterated derivative thereof, a solvate thereof, a solvate of the pharmaceutically acceptable salt thereof or a crystal form thereof according to claim 1, the oxygen-containing heterocyclic compound represented by Formula I has the structure of Formula III:

III

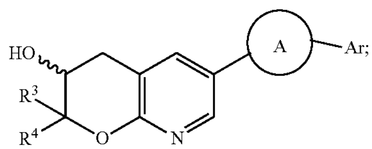

wherein:

Ar and

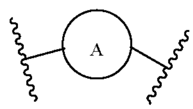

are defined as in the Formula I;

represents , or a mixture of and ; and $R^3$ and $R^4$ are $C_{1-6}$ alkyl substituted with deuterium.

5. The oxygen-containing heterocyclic compound represented by Formula III, the pharmaceutically acceptable salt thereof, deuterated derivative thereof, a solvate thereof, a solvate of the pharmaceutically acceptable salt thereof or a crystal form thereof according to claim 4, the formula III has the following structure:

III'

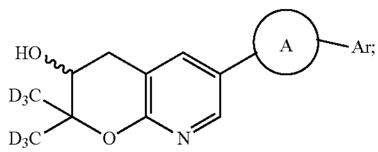

wherein, , Ar and

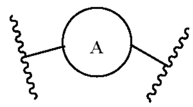

are defined as in the formula III.

6. The oxygen-containing heterocyclic compound represented by Formula II, the pharmaceutically acceptable salt thereof, deuterated derivative thereof, a solvate thereof, a solvate of the pharmaceutically acceptable salt thereof or a crystal form thereof according to claim 2, wherein, Ar is $C_{6-20}$ aryl substituted with one or more $R^{1-1}$, or "5-12 membered heteroaryl containing 1-4 heteroatoms independently selected from O, S and N" substituted with one or more $R^{1-2}$;

$R^{1-1}$ and $R^{1-2}$ are independently selected from halogen and $C_{1-6}$ alkyl;

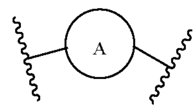

is 5-6 membered heteroaryl containing 1-3 heteroatoms independently selected from O, S and N;

represents or ; and n is 2 or 3.

7. The oxygen-containing heterocyclic compound represented by Formula I, the pharmaceutically acceptable salt thereof, deuterated derivative thereof, a solvate thereof, a solvate of the pharmaceutically acceptable salt thereof or a crystal form thereof according to claim 1, wherein, when Ar is $C_{6-20}$ aryl, or $C_{6-20}$ aryl substituted with one or more $R^{1-1}$, the $C_{6-20}$ aryl and the $C_{6-20}$ aryl in the $C_{6-20}$ aryl substituted with one or more $R^{1-1}$ are $C_{6-10}$ aryl; the $C_{6-10}$ aryl is phenyl or naphthyl;

and/or, when Ar is "5-12 membered heteroaryl containing 1-4 heteroatoms independently selected from O, S and N", or "5-12 membered heteroaryl containing 1-4 heteroatoms independently selected from O, S and N" substituted with one or more $R^{1-2}$, the "5-12 membered heteroaryl containing 1-4 heteroatoms independently selected from O, S and N" and "5-12 membered heteroaryl containing 1-4 heteroatoms independently selected from O, S and N" in the "5-12 membered heteroaryl containing 1-4 heteroatoms independently selected from O, S and N" substituted with one or more $R^{1-2}$ are "5 membered heteroaryl containing 2 heteroatoms selected from N";

and/or, when

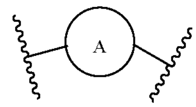

is a 5-6 membered heteroaryl containing 1-3 heteroatoms independently selected from O and N, the

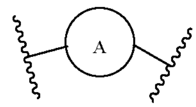

is a 5 membered heteroaryl containing 3 heteroatoms independently selected from O and N;

and/or, when $R^{1-1}$ and $R^{1-2}$ are independently selected from halogen, then the halogen is —F, —Cl, —Br or —I;

and/or, when $R^{1-1}$ and $R^{1-2}$ are independently selected from $C_{1-6}$ alkyl, then the $C_{1-6}$ alkyl is $C_{1-4}$ alkyl, or may be methyl, ethyl, n-propyl, isopropyl, n-butyl, isobutyl, sec-butyl or tert-butyl, or may be methyl;

and/or, when $R^3$ and $R^4$ together with the atom they are attached form $C_{3-8}$ cycloalkyl, then the $C_{3-8}$ cycloalkyl is $C_3$ cycloalkyl, $C_4$ cycloalkyl, $C_5$ cycloalkyl, $C_6$ cycloalkyl, $C_7$ cycloalkyl, or $C_5$ cycloalkyl;

and/or, when $R^3$ and $R^4$ are $C_{1-6}$ alkyl substituted with deuterium, then the $C_{1-6}$ alkyl is $C_{1-4}$ alkyl, or may be methyl, ethyl, n-propyl, isopropyl, n-butyl, isobutyl, sec-butyl or tert-butyl, or may be methyl;

and/or, when $R^3$ and $R^4$ are $C_{1-6}$ alkyl substituted with deuterium, then the $C_{1-6}$ alkyl substituted with deuterium is $—CD_3$.

8. The oxygen-containing heterocyclic compound represented by Formula I, the pharmaceutically acceptable salt thereof, deuterated derivative thereof, a solvate thereof, a solvate of the pharmaceutically acceptable salt thereof or a crystal form thereof according to claim 1, wherein, Ar is

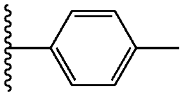,
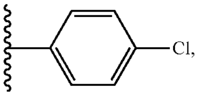

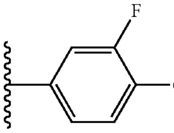 and 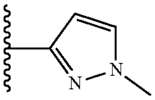; and/or,

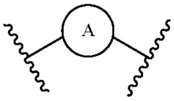 is 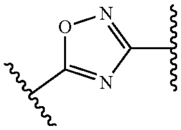 or

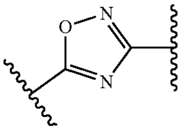; and/or, 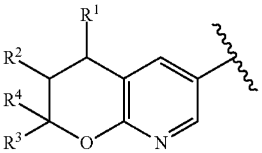 is

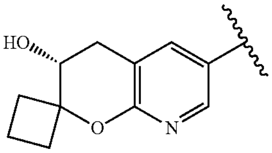, 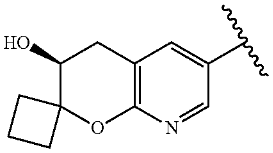,

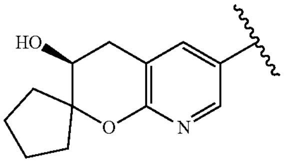 or

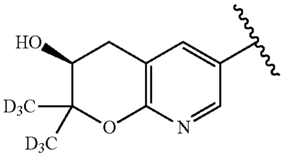.

9. The oxygen-containing heterocyclic compound represented by Formula I, the pharmaceutically acceptable salt thereof, deuterated derivative thereof, a solvate thereof, a solvate of the pharmaceutically acceptable salt thereof or a crystal form thereof according to claim 1, wherein,

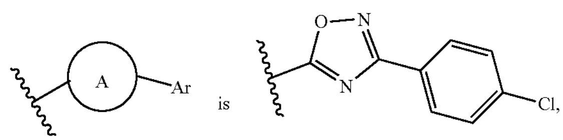

-continued

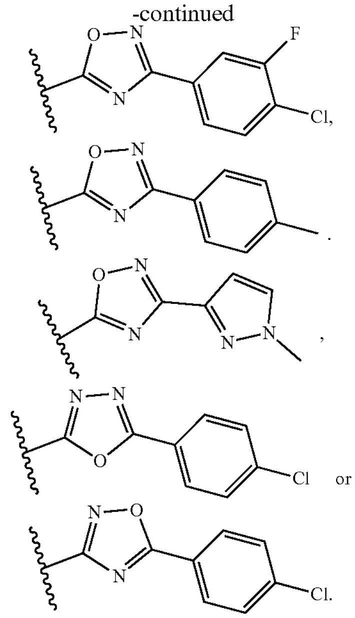

10. The compound, the pharmaceutically acceptable salt thereof, deuterated derivative thereof, solvate thereof, solvate of the pharmaceutically acceptable salt thereof or crystal form thereof according to claim 1 wherein $R^1$ is hydrogen; $R^2$ is selected from hydrogen, deuterium, and hydroxyl; $R^3$ and $R^4$ are $C_{1-6}$ alkyl substituted with deuterium, or, $R^3$ and $R^4$ together with the atom to which they are attached form $C_{3-6}$ cycloalkyl;

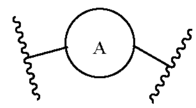

is oxadiazolyl; and Ar is chosen from phenyl substituted with one or more $R^{1-1}$ and pyrazolyl substituted with one or more $R^{1-2}$.

11. The oxygen-containing heterocyclic compound represented by Formula I, the pharmaceutically acceptable salt thereof, deuterated derivative thereof, a solvate thereof, a solvate of the pharmaceutically acceptable salt thereof or a crystal form thereof according to claim 1, wherein, the oxygen-containing heterocyclic compound of Formula I have any one of the following structures:

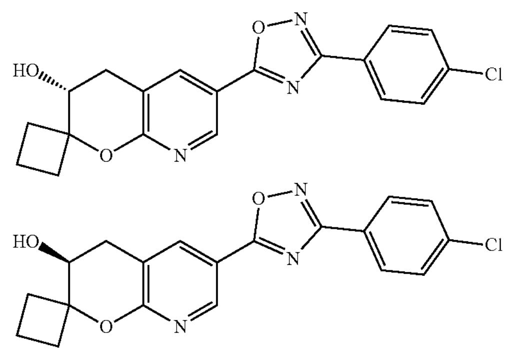

-continued

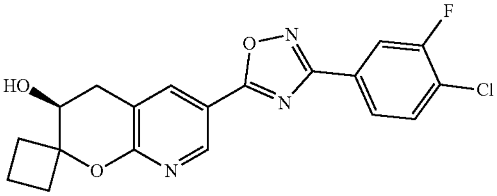

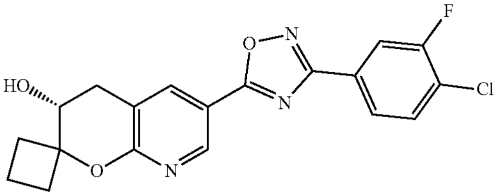

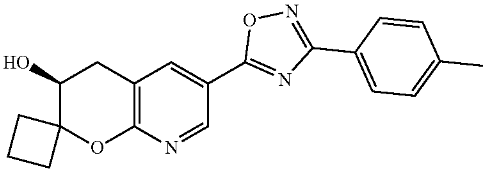

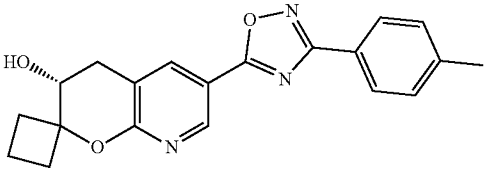

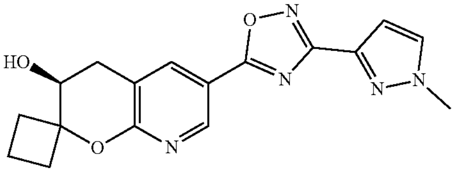

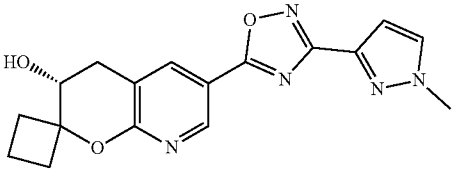

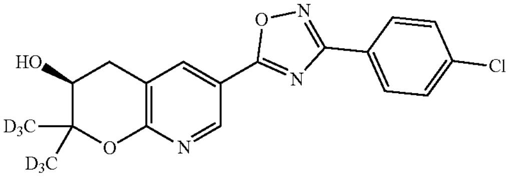

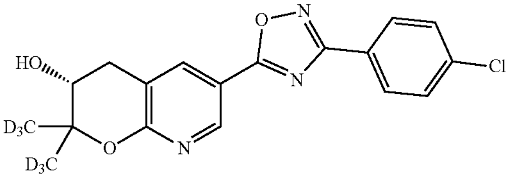

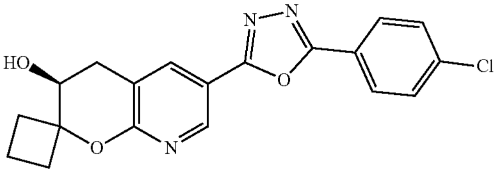

-continued

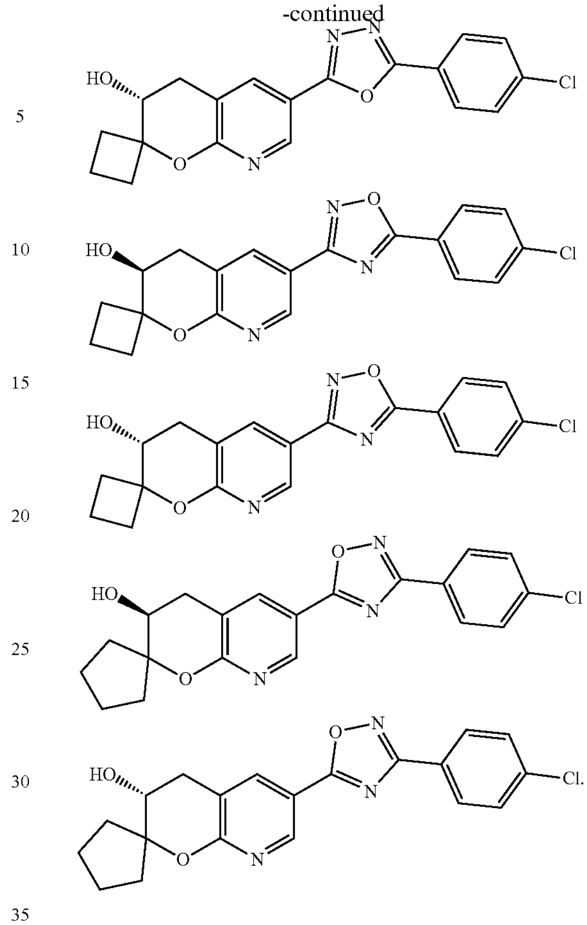

12. A pharmaceutical composition comprising a substance A and a pharmaceutically acceptable excipient, wherein the substance A is a therapeutically effective amount of the oxygen-containing heterocyclic compound represented by Formula I, the pharmaceutically acceptable salt thereof, deuterated derivative thereof, a solvate thereof, a solvate of the pharmaceutically acceptable salt thereof or a crystal form thereof according to claim 1.

13. A method for inhibiting the interaction of homeodomain interacting protein kinase 2 with Smad3, said method comprising combining HIPK2 with a substance A, wherein the substance A is a therapeutically effective amount of the oxygen-containing heterocyclic compound of Formula I, a pharmaceutically acceptable salt thereof, deuterated derivative thereof, a solvate thereof, a solvate of the pharmaceutically acceptable salt thereof or a crystal form thereof according to claim 1.

14. A method for inhibiting Smad3 activation, wherein the method comprising bringing Smad3 into contact with a substance A, wherein the substance A is a therapeutically effective amount of the oxygen-containing heterocyclic compound of Formula I, a pharmaceutically acceptable salt thereof, deuterated derivative thereof, a solvate thereof, a solvate of the pharmaceutically acceptable salt thereof or a crystal form thereof according to claim 1.

15. A method for treating a fibrotic disease comprising administrating a substance A to a subject suffering from a fibrotic disease, wherein the substance A is a therapeutically effective amount of the oxygen-containing heterocyclic compound of Formula I, a pharmaceutically acceptable salt thereof, deuterated derivative thereof, a solvate thereof, a solvate of the pharmaceutically acceptable salt thereof or a crystal form thereof according to claim 1, wherein the disease is renal fibrosis, cardiac fibrosis, hepatic fibrosis, or pulmonary fibrosis.

* * * * *